US009677984B2

(12) United States Patent
Zachariah et al.

(10) Patent No.: US 9,677,984 B2
(45) Date of Patent: Jun. 13, 2017

(54) PULSED-FIELD DIFFERENTIAL MOBILITY ANALYZER SYSTEM AND METHOD FOR SEPARATING PARTICLES AND MEASURING SHAPE PARAMETERS FOR NON-SPHERICAL PARTICLES

(71) Applicant: University of Maryland, College Park, MD (US)

(72) Inventors: Michael R. Zachariah, Potomac, MD (US); Mingdong Li, Germantown, MD (US); George W. Mulholland, Gaithersburg, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 14/611,904

(22) Filed: Feb. 2, 2015

(65) Prior Publication Data
US 2015/0221490 A1 Aug. 6, 2015

Related U.S. Application Data

(60) Provisional application No. 61/934,553, filed on Jan. 31, 2014.

(51) Int. Cl.
*H01J 49/00* (2006.01)
*G01N 15/02* (2006.01)

(52) U.S. Cl.
CPC . *G01N 15/0266* (2013.01); *G01N 2015/0277* (2013.01); *G01N 2015/0288* (2013.01); *G01N 2015/0294* (2013.01)

(58) Field of Classification Search
None
See application file for complete search history.

(56) References Cited

U.S. PATENT DOCUMENTS 5,932,795 A * 8/1999 Koutrakis ............ G01N 1/2205
422/80
7,298,486 B2 * 11/2007 Wang ................. G01N 15/0266
324/71.4
(Continued)

FOREIGN PATENT DOCUMENTS

ES 2126961 A2 * 12/2009 ......... G01N 15/0266
ES 2126961 B1 * 6/2014 ......... G01N 15/0266
(Continued)

OTHER PUBLICATIONS

Alkilany, A. M., Thompson, L. B., Boulos, S. P., Sisco, P. N. and Murphy, C. J. (2012). Gold nanorods: Their potential for photothermal therapeutics and drug delivery, tempered by the complexity of their biological interactions. *Advanced Drug Delivery Reviews* 64:190-199.
(Continued)

*Primary Examiner* — Andrew Smyth
(74) *Attorney, Agent, or Firm* — Carter, DeLuca, Farrell & Schmidt, LLP

(57) ABSTRACT

A method for extracting shape information for particles with similar shape and corresponding system of a tandem differential mobility analyzer (DMA) and pulse field differential mobility analyzer (PFDMA) system, that executes at least generating a steady state aerosol concentration; passing aerosol flow from the aerosol concentration thru a bipolar charger to produce a known charge distribution; passing aerosol thru a DMA with set sheath and aerosol flows and a set voltage to generate a mono-mobility aerosol; passing mono-mobility aerosol thru a PFDMA system; and measuring mobility as a function of electric field by varying the duty cycle of the pulse in the PFDMA system. Alternatively, the method and system relate to separating particles with different shapes by adjusting the duty cycle of the pulse to reach a higher or lower electric field than in the DMA in
(Continued)

which the mono-mobility aerosol was generated; and separating particles based on shape.

8 Claims, 25 Drawing Sheets

(56) References Cited

U.S. PATENT DOCUMENTS

| | | | | |
|---|---|---|---|---|
| 7,518,108 B2* | 4/2009 | Frey | H01J 49/0045 | 250/281 |
| 7,855,360 B2* | 12/2010 | Fernandez de la Mora | G01N 15/0266 | 250/281 |
| 7,931,734 B2* | 4/2011 | Moosmuller | B03C 5/00 | 209/127.1 |
| 8,044,350 B2* | 10/2011 | Chen | G01N 15/0266 | 250/281 |
| 8,192,932 B2* | 6/2012 | Shuman | C07H 21/02 | 435/183 |
| 8,278,622 B2* | 10/2012 | Fernandez de la Mora | G01N 15/0266 | 250/281 |
| 8,378,297 B2* | 2/2013 | Vidal-De-Miguel | G01N 27/624 | 250/281 |
| 8,698,076 B2* | 4/2014 | Orii | G01N 15/0266 | 250/288 |
| 8,919,183 B1* | 12/2014 | Dhaniyala | G01N 15/0266 | 73/28.02 |
| 9,095,793 B2* | 8/2015 | Flagan | B03C 1/30 | |
| 9,138,663 B2* | 9/2015 | Flagan | G01N 15/0266 | |
| 9,207,207 B2* | 12/2015 | Oberreit | G01N 27/622 | |
| 9,239,279 B1* | 1/2016 | Koizumi | G01N 27/622 | |
| 9,297,785 B2* | 3/2016 | Amo | G01N 27/622 | |
| 2005/0153341 A1* | 7/2005 | Alexander | H01J 49/16 | 435/6.12 |
| 2006/0146327 A1* | 7/2006 | Wang | G01N 15/0266 | 356/338 |
| 2007/0102634 A1* | 5/2007 | Frey | H01J 49/0045 | 250/288 |
| 2008/0203290 A1* | 8/2008 | Fernandez de la Mora | G01N 15/0266 | 250/282 |
| 2010/0001184 A1* | 1/2010 | Chen | G01N 15/0266 | 250/307 |
| 2010/0243883 A1* | 9/2010 | Vidal-De-Miguel | G01N 27/624 | 250/282 |
| 2010/0307593 A1* | 12/2010 | Thimsen | B01J 21/063 | 136/263 |
| 2011/0057096 A1* | 3/2011 | Fernandez de la Mora | G01N 15/0266 | 250/282 |
| 2012/0001067 A1* | 1/2012 | Orii | G01N 15/0266 | 250/288 |
| 2012/0325024 A1* | 12/2012 | Vidal-de-Miguel | G01N 27/622 | 73/863.24 |
| 2013/0187042 A1* | 7/2013 | Gillig | G01N 27/624 | 250/283 |
| 2013/0213860 A1* | 8/2013 | Flagan | G01N 15/0266 | 209/143 |
| 2013/0236396 A1* | 9/2013 | Pease, III | A61K 49/0002 | 424/9.1 |
| 2015/0115147 A1* | 4/2015 | Oberreit | G01N 27/622 | 250/282 |
| 2015/0233866 A1* | 8/2015 | Verenchikov | G01N 27/622 | 250/282 |

FOREIGN PATENT DOCUMENTS

| | | | | |
|---|---|---|---|---|
| WO | WO 2008101998 A2 * | 8/2008 | | G01N 15/0266 |
| WO | WO 2008101998 A3 * | 4/2009 | | G01N 15/0266 |

OTHER PUBLICATIONS

Allen, M. D. and Raabe, O. G. (1985). Slip Correction Measurements of Spherical Solid Aerosol-Particles in an Improved Millikan Apparatus. *Aerosol Sci Tech* 4:269-286.

Cheng, M. T., Xie, G. W., Yang, M. and Shaw, D. T. (1991). Experimental Characterization of Chain-Aggregate Aerosol by Electrooptic Scattering. *Aerosol Sci Tech* 14:74-81.

Colbeck, I., Atkinson, B. and Johar, Y. (1997). The morphology and optical properties of soot produced by different fuels. *J Aerosol Sci* vol. 28, No. 5:715-723.

Dahneke, B. E. (1973). Slip correction factors for nonspherical bodies—II free molecule flow. *J Aerosol Sci* vol. 4:147-161.

Flagan, R. C. (2008). Differential Mobility Analysis of Aerosols: A Tutorial. *Kona Powder Part J* 26:254-268.

Guha, S., Li, M., Tarlov, M. J. and Zachariah, M. R. (2012). Electrospray-differential mobility analysis of bionanoparticles. *Trends in Biotechnology* vol. 30, No. 5:291-300.

Kim, S. H., Mulholland, G. W. and Zachariah, M. R. (2007). Understanding ion-mobility and transport properties of aerosol nanowires. *J Aerosol Sci* 38:823-842.

Kousaka, Y., Endo, Y., Ichitsubo, H. and Alonso, M. (1996). Orientation-specific dynamic shape factors for doublets and triplets of spheres in the transition regime. *Aerosol Sci Tech* 24:1, 36-44.

Li, M. (2012). Quantifying Particle Properties from Ion-Mobility Measurements, in *Chemical Physics Program*, Dissertation, University of Maryland, College Park. Available online at: http://hdl.handle.net/1903/13627.

Li, M., Guha, S., Zangmeister, R., Tarlov, M. J. and Zachariah, M. R. (2011a). Quantification and Compensation of Nonspecific Analyte Aggregation in Electrospray Sampling. *Aerosol Sci Tech* 45:7, 849-860. DOI:10.1080/02786826.2011.566901.

Li, M., Guha, S., Zangmeister, R., Tarlov, M. J. and Zachariah, M. R. (2011b). Method for determining the absolute number concentration of nanoparticles from electrospray sources. *Langmuir* 27:14732-14739.

Li, M., Mulholland, G. W. and Zachariah, M. R. (2012). The Effect of Orientation on the Mobility and Dynamic Shape Factor of Charged Axially Symmetric Particles in an Electric Field. *Aerosol Sci Tech*, 46:9, 1035-1044. DOI:10.1080/02786826.2012.686675.

Li, M., You, R., Mulholland, G. W. and Zachariah, M. R. (2013). Evaluating the Mobility of Nanorods in Electric Fields. *Aerosol Sci. Tech.*, 47: 1101-1107.

Li, M.; Mulholland, G. W. and Zachariah, M. R. (2014a ). Understanding the mobility of nonspherical particles in the free molecular regime, *Physical Review E*. 89, 022112.

Li, M.; Mulholland, G. W. and Zachariah, M. R. (2014b). Rotational diffusion coefficient (or rotational mobility) of a nanorod in the free-molecular regime. *Aerosol Sci Tech*. 48:2, 139-141. DOI: 10.1080/02786826.2013.864752.

Ni, W., Kou, X., Yang, Z. and Wang, J. F. (2008). Tailoring longitudinal surface plasmon wavelengths, scattering and absorption cross sections of gold nanorods. *Acs Nano* vol. 2, No. 4:677-686.

Schmid, G. and Chi, L. F. (1998). Metal clusters and colloids. *Adv Mater* 10, No. 7:515-526.

Weiss, R. E., Kapustin, V. N. and Hobbs, P. V. (1992). Chain-Aggregate Aerosols in Smoke from the Kuwait Oil Fires. *J Geophys Res-Atmos* vol. 97, No. D13:14527-14531.

Song, D. K., Lenggoro, I. W., Hayashi, Y., Okuyama, K. and Kim, S. S. (2005). Changes in the shape and mobility of colloidal gold nanorods with electrospray and differential mobility analyzer methods. *Langmuir* 21:10375-10382.

Zelenyuk, A. and Imre, D. (2007). On the effect of particle alignment in the DMA. *Aerosol Sci Tech* 41:2, 112-124. DOI: 10.1080/02786826.2013.819565.

* cited by examiner

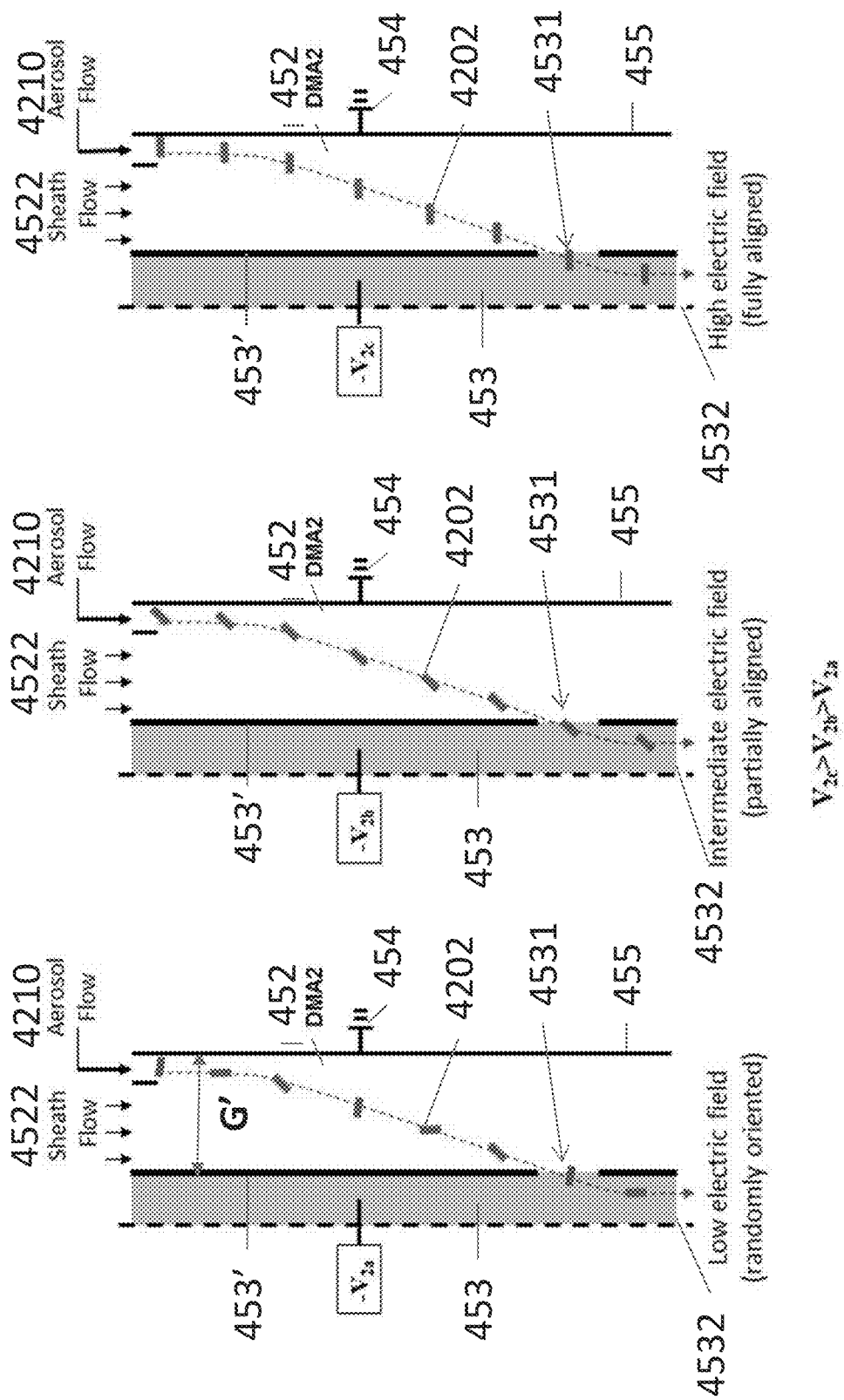
FIG. 5B3
FIG. 5B2
FIG. 5B1

TABLE 1

EXPERIMENTAL CONDITIONS FOR GOLD NANOROD MOBILITY MEASUREMENTS

| | |
|---|---|
| Low electric field ($Q_{sh}$ / $D_{cycle}$ =3 l/min) | 700' DC voltage (duty cycle= 1); $Q_{sh}$ =3 l/min ($Q_a$ =0.07 l/min) |
| Intermediate electric field ($Q_{sh}$ / $D_{cycle}$ =6 l/min) | 704 DC voltage (duty cycle= 1); $Q_{sh}$ =6 l/min ($Q_a$ =0.15 l/min) |
| | 705 Pulsed voltage with duty cycle=50%; $Q_{sh}$ =3 l/min ($Q_a$ =0.07 l/min);5 Hz |
| | 705 Pulsed voltage with duty cycle=50%; $Q_{sh}$ =3 l/min ($Q_a$ =0.07 l/min);10 Hz |
| | 705 Pulsed voltage with duty cycle=50%; $Q_{sh}$ =3 l/min ($Q_a$ =0.07 l/min);100 Hz |
| | 705 Pulsed voltage with duty cycle=50%; $Q_{sh}$ =3 l/min ($Q_a$ =0.07 l/min);500 Hz |
| High electric field ($Q_{sh}$ / $D_{cycle}$ =12 l/min) | 701 DC voltage (duty cycle= 1); $Q_{sh}$ =12 l/min ($Q_a$ =0.3 l/min) |
| | 703 Pulsed voltage with duty cycle=50%; $Q_{sh}$ =6 l/min ($Q_a$ =0.15 l/min);5 Hz |
| | 703 Pulsed voltage with duty cycle=50%; $Q_{sh}$ =6 l/min ($Q_a$ =0.15 l/min);10 Hz |
| | 703 Pulsed voltage with duty cycle=50%; $Q_{sh}$ =6 l/min ($Q_a$ =0.15 l/min);100 Hz |
| | 703 Pulsed voltage with duty cycle=50%; $Q_{sh}$ =6 l/min ($Q_a$ =0.15 l/min);500 Hz |
| | 702 Pulsed voltage with duty cycle=25%; $Q_{sh}$ =3 l/min ($Q_a$ =0.07 l/min);5 Hz |
| | 702 Pulsed voltage with duty cycle=25%; $Q_{sh}$ =3 l/min ($Q_a$ =0.07 l/min);10 Hz |
| | 702 Pulsed voltage with duty cycle=25%; $Q_{sh}$ =3 l/min ($Q_a$ =0.07 l/min);100 Hz |
| | 702 Pulsed voltage with duty cycle=25%; $Q_{sh}$ =3 l/min ($Q_a$ =0.07 l/min);500 Hz |

START — 1301

For particles with similar shape to apply tandem DMA-PFDMA system to "extract shape information" — 1302

Generate a steady state aerosol concentration — 1304

Pass aerosol concentration thru a bipolar charger (neutralizer) to produce a known charge distribution Pass the aerosol thru a DMA with set sheath and aerosol flows and a set voltage to generate a mono-mobility aerosol — 1306

Pass the mono-mobility aerosol thru a PFDMA system — 1308

1401 START
For particles with different shapes, applying tandem DMA-PFDMA to "separate particles based on their shape"

1402 Generate a steady state aerosol concentration

1404 Pass aerosol with different shapes thru a bipolar charger (neutralizer) to produce a known charge distribution

1406 Pass the aerosol thru DMA with set sheath and aerosol flows and a set voltage to generate a mono-mobility aerosol

1408 Pass the mono-mobility aerosol thru the PFDMA

```
                    ┌──────────────────────────────────────────────┐
                    │ Calibrate DMAs using standard polystyrene    │
              1502──│ latex (PSL) spheres so that the particle     │
                    │ mobility is accurately known to enable       │
                    │ accurate measurement of small changes in     │
                    │ the mobility                                 │
                    └──────────────────────────────────────────────┘
                            │
                    ┌──────────────────────────────────────────────┐
                    │ Calibrate PFDMA using standard polystyrene   │
              1504──│ latex (PSL) spheres for validating           │
                    │ performance of PFDMA (mobility should be     │
                    │ independent of pulse frequency)              │
                    └──────────────────────────────────────────────┘
                            │
                    ┌──────────────────────────────────────────────┐
              1506──│ Generate a steady state aerosol concentration│
                    └──────────────────────────────────────────────┘
                            │
                    ┌──────────────────────────────────────────────┐
              1508──│ Pass aerosol thru a bipolar charger          │
                    │ (neutralizer) to produce a known charge      │
                    │ distribution                                 │
                    └──────────────────────────────────────────────┘
```

1514A — Cont. from FIG. 15B
For particles with similar shape, applying tandem DMA-PFDMA to "extract shape information";

1516A — Measure mobility as a function of electric field by varying the duty cycle of the pulse in the PFDMA 1518A — Fit the measured mobility data at various electric fields to orientation-averaged mobility model to obtain the shape information

FIG. 15C

Cont. from FIG. 15D

1514B — For particles with different shapes, applying tandem DMA-PFDMA to "separate particles based on their shape"

1516B — Adjust the duty cycle of the pulse in the PFDMA to reach a higher or lower electric field than the previous DMA 1518B — Separate particles based on their shape

FIG. 15D

PULSED-FIELD DIFFERENTIAL MOBILITY ANALYZER SYSTEM AND METHOD FOR SEPARATING PARTICLES AND MEASURING SHAPE PARAMETERS FOR NON-SPHERICAL PARTICLES

CROSS-REFERENCE TO RELATED APPLICATIONS

This application claims the benefit of, and priority to, U.S. Provisional Patent Application 61/934,553 "DEVELOPMENT OF A PULSED-VOLTAGE DIFFERENTIAL MOBILITY ANALYZER", by M. Zachariah et al., filed on Jan. 31, 2014, the entire contents of which are incorporated herein by reference.

GOVERNMENT SUPPORT

This invention was made with U.S. government support under 70NANB9H9199 awarded by the National Institute of Standards and Technology (NIST). The U.S. government has certain rights in this invention.

BACKGROUND

1. Technical Field

This disclosure relates to differential mobility analyzers and more particularly to differential mobility analyzers that yield a mobility-equivalent spherical diameter.

2. Description of Related Art

Nanomaterials are widely applied and studied in medicine, electronics, biomaterials and environmental science. Effective measurement and accurate characterization of nanomaterials play a critical role in the development of nanotechnology. It is well-known that many of the properties of particles are size dependent. Moreover, for aspherical structures such as nanorods, nanowires, the properties are also greatly influenced by their shapes.

For example gold nanorods are useful for the formation of many functional composite materials due to their special light scattering and absorption properties (Ni et al. 2008; Alkilany et al. 2012). Non-spherical particles also have important effects on environment and human health. Soot aggregates produced by combustion are highly non-spherical ramified structures with non-integer fractal dimensions. The common feature of all these materials is that they are non-spherical and thus cannot be dimensionally characterized by just one length scale. To obtain size and shape information of nanoparticles, microscopy techniques, such as transmission or scanning electron microscopy (TEM/SEM), are traditionally applied. However, in these off-line methods, good sampling methods and time-consuming operations are needed for a precise distribution measurement. It is also reported that the sampling and imaging process itself may cause coalescence of small clusters (Schmid and Chi 1998).

One of the major challenges in particle online measurement is to extend the dimensionality measurement beyond the assumption of spherical symmetry. For a nonspherical particle, a differential mobility analyzer (DMA) measurement yields a mobility-equivalent spherical diameter, but provides no information about the degree of sphericity.

The differential mobility analyzer (DMA) is the gold-standard on-line measurement method for obtaining a complete electrical-mobility-size distribution of nanoparticles in the aerosol phase (Flagan 2008). For a spherical particle, the electrical mobility diameter is equivalent to its geometric diameter. However, if the particle is non-spherical, the resulting electrical mobility diameter is that diameter for a sphere with the same mobility as the analyte particle. For example Song et al. (Song et al. 2005) investigated the relationship between the electrical mobility size and particles shape, by changing the particle shape from nanorod to sphere by heating the particles from 25° C. to 800° C., and showed that the mobility diameters decreased from 55 nm to 25 nm. Since the mobility size measured in the DMA depends on the drag force on the particles, thus for a non-spherical particle, mobility necessarily depends on orientation with respect to the applied electric field (Kousaka et al. 1996; Zelenyuk and Imre 2007; Kim et al. 2007; Li et al. 2012; Li et al. 2013). In principle then, an orientation dependent mobility measurement should yield some information on particle shape.

Kousaka et al. (1996) measured the dynamic shape factor for doublets of uniform spheres (Polystyrene latex particles; PSL) in the transition regime and pointed out that the orientation of doublets is a function of electric field in the DMA and the size of doublets. Zelenyuk and Imre (2007) applied this idea to more aspherical particles and showed that the dependence of electrical mobility size on electric field can be applied to separate particles based on their shape. Kim et al. (2007) measured the length of carbon nanotubes considering a scalar expression of drag force.

SUMMARY

The embodiments of the present disclosure provide a novel and non-obvious solution to the problems of differentiating between particles of similar shape and of separating particles having different shapes.

More particularly, the embodiments of the present disclosure relate to a method for extracting shape information for particles with similar shape and a corresponding system of a tandem differential mobility analyzer (DMA) and pulse field differential mobility analyzer (PFDMA) system, that executes at least generating a steady state aerosol concentration; passing the aerosol flow from the aerosol concentration thru a bipolar charger to produce a known charge distribution passing the aerosol thru a DMA with set sheath and aerosol flows and a set voltage to generate a mono-mobility aerosol; passing the mono-mobility aerosol thru a PFDMA system; and measuring mobility as a function of electric field by varying the duty cycle of the pulse in the PFDMA system.

The embodiments of the present disclosure relate to a method for separating particles with different shapes and a corresponding system of a tandem differential mobility analyzer (DMA) and pulse field differential mobility analyzer (PFDMA) system, that executes at least generating a steady state aerosol concentration; passing the aerosol flow from the aerosol concentration thru a bipolar charger to produce a known charge distribution; passing the aerosol thru a DMA with set sheath and aerosol flows and a set voltage to generate a mono-mobility aerosol; passing the mono-mobility aerosol thru a PFDMA system; adjusting the duty cycle of the pulse in the PFDMA to reach a higher or lower electric field than in the DMA in which the mono-mobility aerosol was generated; and separating particles based on their shape.

The embodiments of the present disclosure relate to a method for operating a pulse field differential mobility analyzer (PFDMA) system, and a pulse field differential mobility analyzer (PFDMA) system that executes at least passing an aerosol through a PFDMA system; creating a pulse electric field in the PFDMA via a pulser system; executing processor software to implement scanning as voltage steps of DC voltage from the pulser system; and generating a square electrical pulse with rapid rise and fall, and small drop off over the range of voltages of interest via the pulser system.

BRIEF DESCRIPTION OF THE DRAWINGS

These and other advantages will become more apparent from the following detailed description of the various embodiments of the present disclosure with reference to the drawings wherein:

FIG. 5B1 is a schematic diagram according to embodiments of the present disclosure of the trajectories of particles with similar shape entering the DMA of a PFDMA system at a low electric field such that the particles remain randomly oriented with respect to the electric field of the DMA;

FIG. 5B2 is a schematic diagram according to embodiments of the present disclosure of the trajectories of particles with similar shape entering the DMA of a PFDMA system at an intermediate electric field such that the particles become partially aligned with respect to the electric field of the DMA;

FIG. 5B3 is a schematic diagram according to embodiments of the present disclosure of the trajectories of particles with similar shape entering the DMA of a PFDMA system at a high electric field such that the particles become aligned with respect to the electric field of the DMA;

FIG. 7 illustrates Table 1 according to embodiments of the present disclosure of experimental conditions for gold nanorod mobility measurements;

FIG. 13A is a block diagram of the method according to embodiments of the present disclosure of general steps of applying the tandem DMA and PFDMA system of FIGS. 5, 5A and 5B1, 5B2, 5B3 to particles of similar shape to extract shape information;

FIG. 14A is a block diagram of the method according to embodiments of the present disclosure of general steps of applying the tandem DMA and PFDMA system of FIGS. 10, 10A and 10B to particles of different shapes to separate particles based on their shape;

FIG. 15A is a block diagram of the method according to embodiments of the present disclosure of detailed steps of applying the tandem DMA and PFDMA system of FIGS. 5, 5A and 5B1, 5B2, 5B3 and of FIGS. 10, 10A and 10B;

FIG. 15C is a continuation of the block diagram of FIG. 15B for particles with similar shape to extract shape information by applying the tandem DMA and PFDMA system of FIGS. 5, 5A and 5B1, 5B2, 5B3;

FIG. 15D is a continuation of the block diagram of FIG. 15B for particles with different shapes to separate particles based on their shape by applying the tandem DMA and PFDMA system of FIGS. 10,10A and 10B;

DETAILED DESCRIPTION

Figure 1:
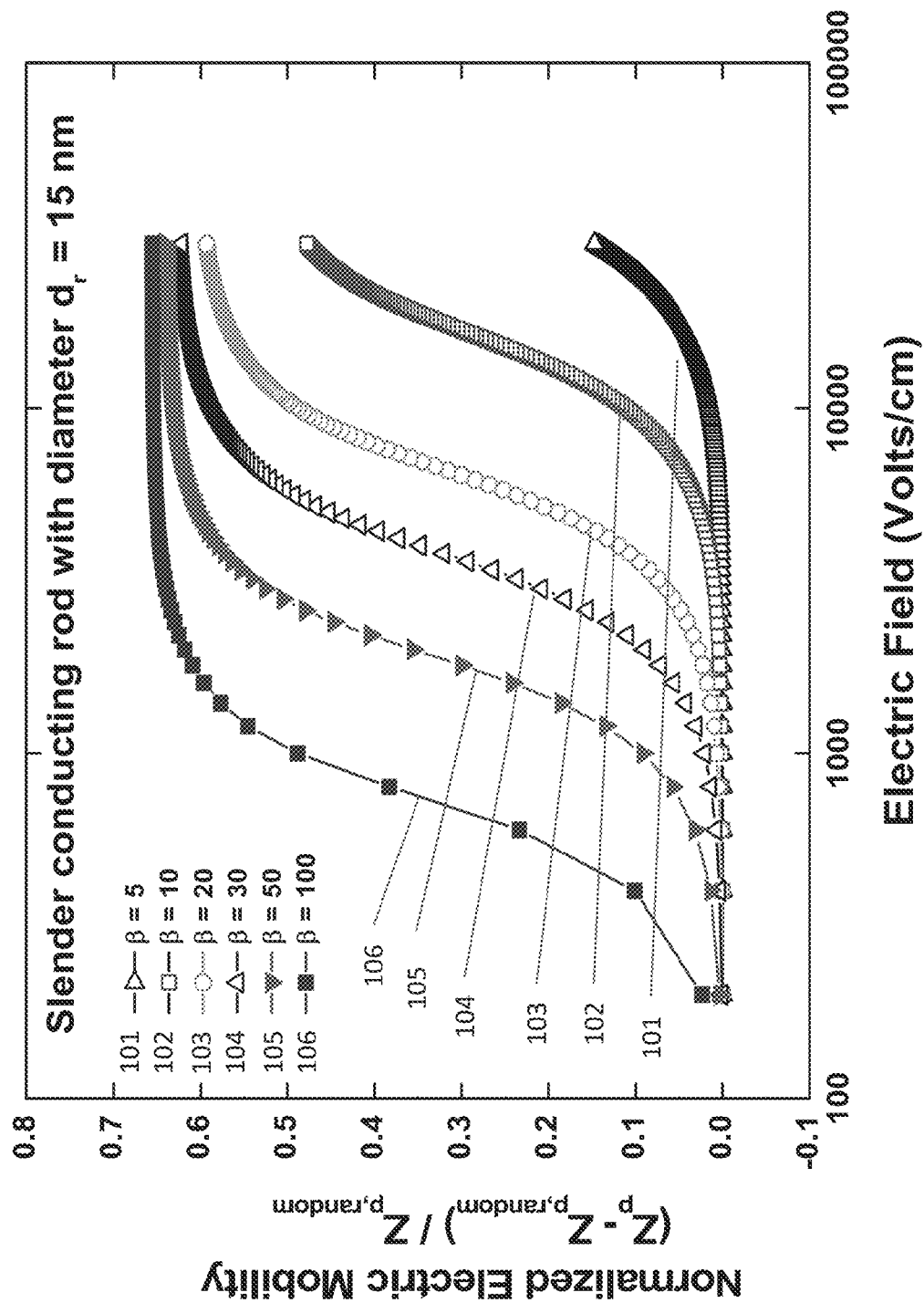
FIG. 1 is a graphical plot of a theoretical calculation according to embodiments of the present disclosure of the effect of electric field on the scaled mobility (relative to the mobility for a randomly oriented rod) for various aspect ratio slender conducting rod with rod diameter $d_r$=15 nm. Mobility is calculated in the free molecular regime using Dahneke's expression (Eqns. 3-1; 3-2). 30,000 Volts/cm is the air breakdown limit.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The word "exemplary" is used herein to mean "serving as an example, instance, or illustration." Any embodiment described herein as "exemplary" is not necessarily to be construed as preferred or advantageous over other embodiments.

It is to be understood that the method steps described herein and claimed in the claim below need not necessarily be performed in the order as described. Further, words such as "thereafter," "then," "next," etc., are not intended to limit the order of the steps. These words are simply used to guide the reader through the description of the method steps.

The implementations described herein may be implemented in, for example, a method or a process, an apparatus, a software program, a data stream, or a signal. Even if only discussed in the context of a single form of implementation (for example, discussed only as a method), the implementation of features discussed may also be implemented in other forms (for example, an apparatus or program). An apparatus may be implemented in, for example, appropriate hardware, software, and firmware. The methods may be implemented in, for example, an apparatus such as, for example, a processor, which refers to processing devices in general, including, for example, a computer, a microprocessor, an integrated circuit, or a programmable logic device. Processors also include communication devices, such as, for example, computers, cell phones, tablets, portable/personal digital assistants, and other devices that facilitate communication of information between end-users within a network.

The general features and aspects of the present disclosure remain generally consistent regardless of the particular purpose. Further, the features and aspects of the present disclosure may be implemented in system in any suitable fashion, e.g., via the hardware and software configuration of system or using any other suitable software, firmware, and/or hardware. For instance, when implemented via executable instructions, such as the set of instructions, various elements of the present disclosure are in essence the code defining the operations of such various elements. The executable instructions or code may be obtained from a computer-readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

For a non-spherical particle, a differential mobility analyzer (DMA) measurement yields a mobility-equivalent spherical diameter, but provides no information about the degree of sphericity. However given that the electrical mobility for non-spheres is orientation dependent, and that orientation can be manipulated using electric fields of varying strength, one can in principle extract some type of shape information through a systematic measurement of mobility as a function of particle orientation. Here we describe the development of a pulsed field differential mobility analyzer (PFDMA) which enables one to change the peak E-field experienced by the particle to induce orientation, while still maintaining the same time averaged field strength as a DMA experiment. The instrument is validated with PSL spheres with accurately known size, and gold rods with dimensions accurately determined by TEM. We demonstrate how the instrument can be used for particle separation and extraction of shape information. In particular we show how one can extract both length and diameter information for rod-like particles. This generic approach can be used to obtain dynamic shape factors or other multi-variate dimensional information (e.g. length and diameter).

In the studies of Li et al., (2012; 2013), in order to present the appropriate relationship between the measured electrical mobility size (or detection voltage) and the geometric shape of particles, an orientation-averaged electrical mobility theory for rigid axisymmetric particles undergoing Brownian motion has been developed by considering the electrical polarization of the particles in an electric field. This theory was validated by experimental results of well-defined doublets of NIST (National Institute of Standards and Technology-U.S. Department of Commerce) traceable size standard PSL spheres (127 nm, 150 nm, 200 nm and 240 nm) (Li 2012) and monodisperse gold rods (Li et al. 2013). This model (which requires information on the friction coefficient tensor) has been further extended to any particle shape in a systematic study of the mobility of non-spherical particles (Li2014a). The particle geometric shape information can then be extracted from experimental mobility measurements at various electric fields by fitting Li's theory (Li et al. 2013).

In the previous studies, the way of measuring the particle mobility at various electric fields is to vary the sheath flow in the DMA. However, changing flow is not convenient and in so doing the instrument resolution is also changed. A major advantage of the PFDMA is that it enables changing the electric field without changing the flow by using a pulsed field so one can obtain a higher field yet the same average field. There is the advantage of obtaining particle mobility results by changing the duty cycle rather than the flow, which is a significantly more convenient method. Varying of the duty cycle maintains the same resolution and is more convenient than varying flow.

Thus, the embodiments of the present disclosure relate to a DMA wherein changing the electric field can be performed without changing the flow by using a pulsed field, which is a much more convenient way, so one can obtain a higher field yet the same average field.

1. System Features

Given that the electrical mobility for nonspheres is orientation-dependent, and that orientation can be manipulated using electric fields of varying strength, one can, in principle, extract shape information through a systematic measurement of mobility as a function of particle orientation. Therefore, the present disclosure relates to a pulsed-field differential mobility analyzer (PFDMA) system which enables one to change the peak E-field experienced by the particle to induce orientation, while still maintaining the same particle transit time. The PFDMA system obtains the shape information by measuring the electrical mobility under different electric fields. The PFDMA system is validated with polystyrene latex (PSL) spheres with accurately known size, and gold rods with dimensions accurately determined by transmission electron microscopy (TEM). The system can be used for particle separation and extraction of shape information. In particular, both length and diameter information can be extracted for rod-like particles. Furthermore, the system can be applied to aggregates which are the most important class of non-spherical particles. The mobility size of soot non-spherical aggregates shows a clear alignment effect. Since the mobility size of spheres is constant, the experimental results demonstrate that PFDMA can be used to separate spherical particles from non-spherical aggregates. This generic approach can be used to obtain shape information for non-spherical particles and separate particles based on their shape. In this disclosure, the shorthand expression PFDMA may be utilized to refer to the PFDMA system described above.

Pulsed electric fields have been previously used for measuring the light scattering by aligned and randomly oriented agglomerate particles (Cheng et al. 1991; Weiss et al. 1992; Colbeck et al. 1997); however, this is the first application for the electric mobility of a particle. This new method enables one to change the peak E-field experienced by the particle, while still maintaining the same time averaged field. In so doing one could in principle systematically change the average orientation of a non-spherical particle and thus its mobility without varying the flow rates in the measurement setup. The instrument is tested on PSL spheres and gold nanorods with known size and shape (conducting monodisperse non-spheres), and the result shows that the PFDMA can be used for particle separation and particle shape information measurements. Long slender gold nanorods were chosen because the cylindrical shape is one of the few non-spherical shapes where there is an exact solution in the free molecular limit and because the shape affect is most pronounced for a shape with a large aspect ratio. Another key experimental factor was the monodispersity of the rods in terms of diameter and length. A final important feature is the high conductivity of the gold nanorod.

The PFDMA consists of two components, a pulser system connected to a DMA. The pulser system, shown in FIG. 4, generates square-wave high-voltage pulses. The output of this pulser system is then connected to a DMA for its voltage input. Different models of DMA can measure different range of particle size. Generally speaking, the PFDMA can apply to any model of DMA. In this article, the PFDMA is demonstrated and validated below using two commercial available models of DMA, which we refer to as a short DMA (for smaller particle sizes) and a long DMA (larger particle sizes). However, the applications of PFDMA are not restricted to those particular DMA models. The pulser system, which generates square-wave high-voltage pulses for the DMA's voltage input, has three components as in FIG. 4, a pulse generator, a gate signal source, and a DC power supply. The pulse generator has two inputs, one is connected to the gate signal source and another is connected to the DC power supply. The pulse generator has one output, which is also the output of the pulser system. This output provides high voltage pulses and is connected to a DMA for its voltage input. The duty cycle and frequency of the generated high voltage pulse are controlled by the gate signal source. And the height of the generated high voltage pulse is controlled by the DC voltage supply. When the voltage output of the DC voltage supply is changed, the height of the generated high voltage pulse is also changed accordingly.

Figure 5:
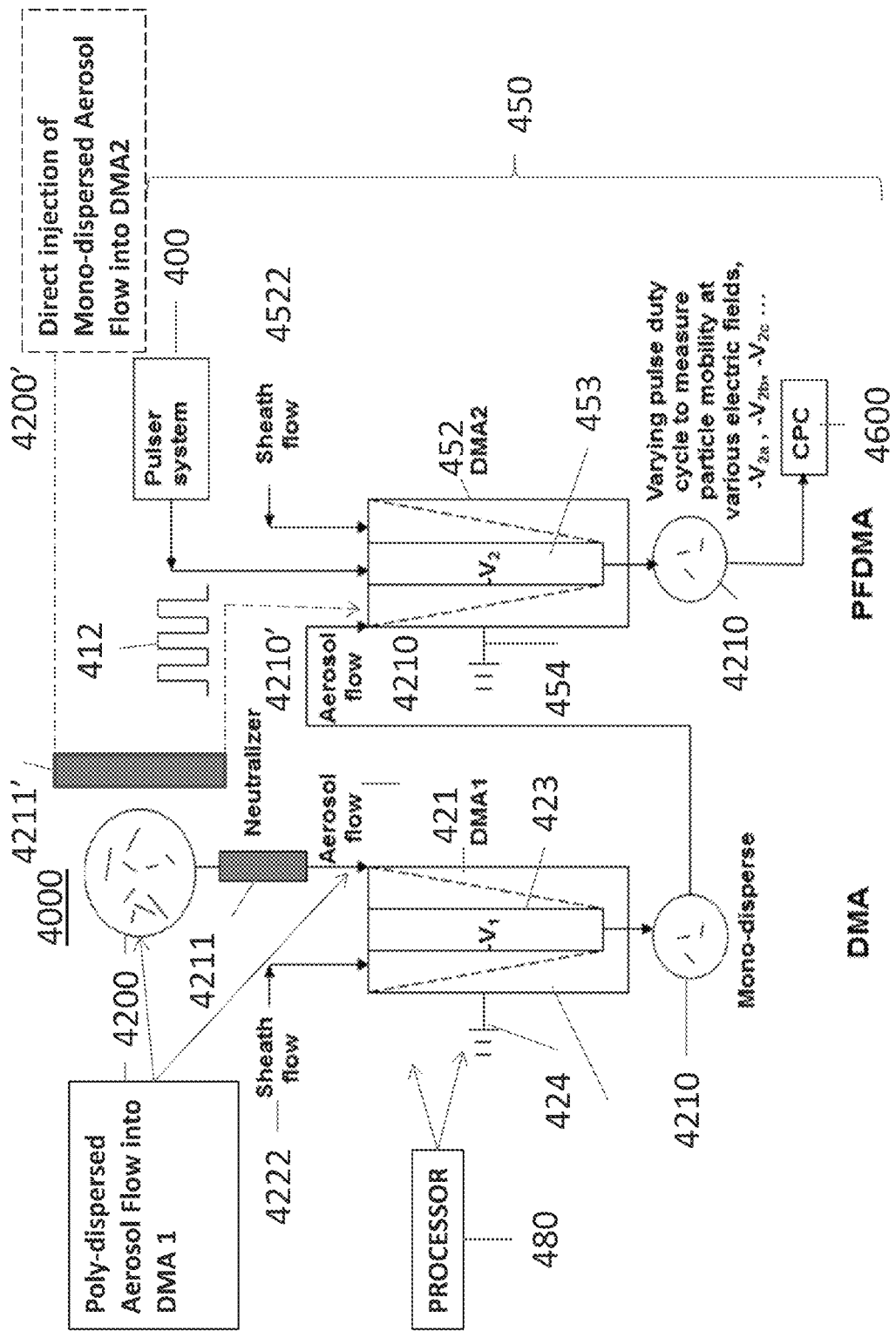
FIG. 5 is a schematic diagram according to embodiments of the present disclosure of a tandem DMA and pulse field differential mobility analyzer (PFDMA) system that includes a DMA that selects mono-dispersed particles and a PFDMA system that measures particle mobility at various electric fields according to embodiments of the present disclosure.
Figure 10:
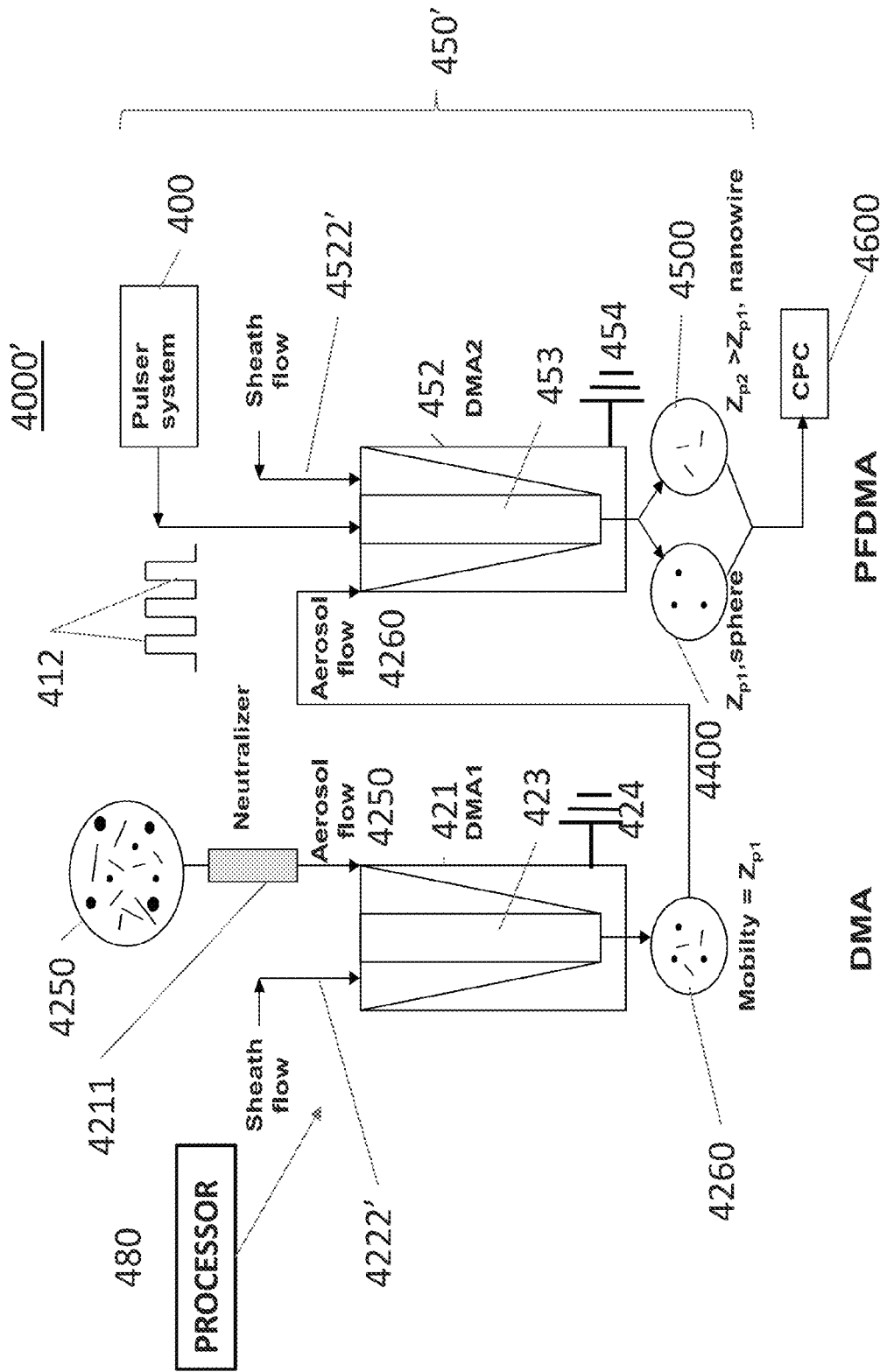
FIG. 10 is a schematic diagram according to embodiments of the present disclosure of a tandem DMA and pulse field differential mobility analyzer (PFDMA) system that includes a DMA to select mono-mobility particles fluidically coupled to a pulsed field DMA system to separate spheres from nanowires.

There are two applications (or modes of operation) of this PFDMA demonstrated in the present disclosure. One is extracting particle geometric shape information from pulsed mobility measurements, and the other is separating particle based on their shapes using PFDMA. Both applications can use the same setup as shown in FIG. 5 or FIG. 10. If the particles are poly-dispersed, a DMA as DMA1 in FIG. 5 is necessary to size-select particles and make the particle monodispersed, then a PFDMA applies for the application of "extracting particle geometric shape information". However, if the particles are monodispersed, there is no need for a DMA as DMA 1 in FIG. 5 to pre-select the particles for this application. A sole PFDMA is adequate to extracting particle shape information as we will demonstrate in section 4.3 below where Au-nanorods are monodispersed.

Once data are measured using a PFDMA, a data analysis algorithm based on the particle mobility theory disclosed herein is still needed to 'extraction of particle shape information', for example, to obtain the length and diameter of a gold rod. A least-squares fitting procedure has been demonstrated to extract diameter and length of the gold rods by use of the model and the experimental data measured by a PFDMA as described and illustrated below.

2. Theoretical Models For Shape Measurement

The particle electrical mobility, $Z_p$, is defined by: $Z_p = v_r / E$, where $v_r$ is the particle drift velocity and E is the magnitude of the electric field. By equating the electrostatic attraction force to the drag force on a spherical particle, electrical mobility, $Z_p$ can be obtained as:

$$Z_p = \frac{neC_c(d_m)}{3\pi\eta d_m} \quad (1)$$

where n is the number of elementary charges on the particle, $d_m$ the electrical mobility diameter, and $C_c(d_m)$ the Cunningham Slip Correction Factor, which was parameterized by Allen and Raabe (1985). The electrical mobility diameter $d_m$ of a sphere is equal to its geometric diameter, and the electrical mobility $Z_p$ is only a function of this spherical diameter based on Eqn. (1) and independent of electric field in the DMA. However, for a non-spherical particle, $d_m$ is the equivalent diameter of a sphere having the same drag force, and the size and shape information of this non-spherical particle is contained in the electrical mobility, $Z_p$. Unlike a spherical particle for which the electrical mobility is independent of field strength, the non-spherical particle, because of its field dependent orientation, has a field dependent mobility $Z_p$ (Shape, E).

For non-spherical particles, Eqn. (1) can be used to get an equivalent spherical diameter, but is not sufficient to obtain the geometric shape information. Li et al. (2012) presented a general form shown below for the orientation-averaged mobility for an axisymmetric particle in an electric field which has been validated by experimental results of doublets with primary particle size larger than 125 nm (Li 2012) and of gold nanorods (Li et al. 2013), $$\overline{Z}_p = q[K_\perp^{-1} + (K_\square^{-1} - K_\perp^{-1})<\cos^2\theta>] \quad (2)$$

where q is the net charge on the particle, $K_\perp$ is the principal component of the friction coefficient tensor perpendicular to the axial direction, $K_\square$ is the component parallel to the axial direction, $$<\cos^2\theta> = \int_0^\pi \cos^2\theta f(\theta)\sin\theta d\theta,$$

is the orientationally-averaged $\cos^2(\theta)$, which is a function of the electric field strength which leads to the E dependence of the average mobility and $f(\theta)$ is the orientational probability function with $$\int_0^\pi f(\theta)\sin\theta d\theta = 1$$

The evaluation of Eqn. (2) requires a knowledge of $K_\perp$ and $K_\square$, which depend on drag model ($\vec{F}_{drag} = -\hat{K} \cdot \vec{V}_d$) specific to the geometry of interest (e.g. ellipsoid, rod, doublets of spheres), and the orientation average value $<\cos^2 \theta>$. The detail calculations of $K_\perp$ and $K_\square$ for nanorods and ellipsoids in the three regimes, and the calculations of $<\cos^2 \theta>$ were shown in Li et al. (2012). Combining the orientation-averaged mobility expression and the experimental measured mobility, one can obtain particle shape information.

Orientation-Averaged-Mobility for a Slender Conducting Rod in the Free Molecular Regime.

The friction coefficients, $K_\square$ and $K_\perp$ in Eqn. (2) are given by (Li et al., 2012 Eqn. A1, A2) for a rod (length $L_r$, diameter $d_r$, aspect ratio $\beta = L_r/d_r$) in the free molecular regime (where the gas viscosity, $\eta = 1.8325 \times 10^{-5}$ kg m$^{-1}$ s$^{-1}$; the mean free path of gas, $\lambda = 67.3$ nm; the momentum accommodation, $f = 0.9$ used in this work (Dahneke 1973))

$$K_0 = \frac{\pi \eta d_r^2}{2\lambda}\left[\left(\beta + \frac{\pi}{4} - 1\right)f + 2\right] \quad (3\text{-}1)$$

$$K_\perp = \frac{\pi \eta d_r^2}{2\lambda}\left[\left(\frac{\pi-2}{4}\beta + \frac{1}{2}\right)f + 2\beta\right] \quad (3\text{-}2)$$

and $<\cos^2\theta>$ is given by (Li et al., 2012, Eqn. 22) for a conducting rod using the induced dipole polarization energy, $$\langle\cos^2\theta\rangle = \frac{1}{2\delta}\left[\frac{2\sqrt{\delta}\,e^\delta}{\sqrt{\pi}\,Erfi(\sqrt{\delta})} - 1\right] \quad (4)$$

where $$\delta = \frac{(\alpha_0 - \alpha_\perp)E^2}{2kT}$$

$\alpha_0$, $\alpha_\perp$ are the two principal components of polarizability, $$Erfi(z) = \frac{2}{\sqrt{\pi}}\int_0^z e^{t^2}dt,$$

is the imaginary error function.

Evaluation of the mobility expression (Eqn. (2)) is mathematically simplified by making a slender conducting rod approximation (length $L_r$, diameter $d_r$, aspect ratio $\beta = L_r/d_r \gg 1$) for the values of polarizability ($\alpha_\square$, $\alpha_\perp$) in Eqn. (4), (Li et al. 2013)

$$\alpha_0 = \frac{\varepsilon_0 \pi d_r^3 \beta^3}{4[\ln(2\beta) - 1]}, \quad \alpha_\perp = \frac{\varepsilon_0 \pi d_r^3 \beta}{2}, \quad (5)$$

$\epsilon_0$ is free-space permittivity, E is the intensity of electric field and k is the Boltzmann constant (T=296.15 K used in this work). The deviation of $\delta$ for $\beta$=16 between the value given by the slender approximation (5) and given by the full theory (Li et al., 2012, Eqn. A13, A14) is about 0.66%.

At low field strengths, the thermal energy dominates the aligning energy, and Brownian dynamics results in a random orientation. As the electric field increases, the slender rod will tend to align and result in a larger electric mobility.

FIG. 1 is a graphical plot of a theoretical calculation of the effect of electric field on the scaled mobility (relative to the mobility for a randomly oriented rod) for various aspect ratio slender conducting rod with rod diameter $d_r$=15 nm. Mobility is calculated in the free molecular regime using Dahneke's expression (Eqns. 3-1; 3-2). 30,000 Volts/cm is the air breakdown limit.

In FIG. 1, the normalized (relative to random orientation) electrical mobility $$(Z_p - Z_{p,random})/Z_{p,random}$$

is plotted vs. applied electric field (Volts/cm) of a slender conducting rod (calculated in free molecular regime with Eqns. (2), (3), (4) (5)) (Li et al. 2012; 2013) for a wide range of aspect ratios, $\beta$, and with diameter $d_r$=15 nm. The range of aspect ratios $\beta$ include $\beta$=5 (plot 101), $\beta$=10 (plot 102), $\beta$=20 (plot 103), $\beta$=30 (plot 104), $\beta$=50 (plot 105) and $\beta$=100 (plot 106). A clear increase in mobility is observed with increasing field strength for all aspect ratios. The onset of alignment occurs at lower field strength with increasing $\beta$. The sigmoidal shape of the curves is key to being able to size nanowires and separate them from spheres.

In section 4.3, it is shown that least-squares fitting can be used to extract both the diameter and the length of gold rods from the experimental mobility measurements in various electric fields using Eqs. (2), (3-1), (3-2), (4) and (5).

3. Pulsed Field Differential Mobility Analyzer (Pfdma)

The shape information for a non-spherical particle is contained in the electrical mobility as shown in Eqn. (2), which is usually a nonlinear function of electric field and particle shape. Once the mobility is measured from a DMA at various electric field magnitudes, one can fit Eqn. (2) to extract the particle shape information.

One way of measuring the effect of particle alignment under different electric fields is to vary the sheath flow in the DMA. However, changing flow is not very convenient, and in so doing the instrument resolution is also changed. An instrumental technique according to embodiments of the present disclosure employs a Pulsed DMA, which allows one to change the electric field acting on the non-spherical particle by only changing the duty cycle of a pulsed electric field in a DMA rather than changing the flow. This technique also allows one to employ very high fields, to induce orientation increasing mobility), while keeping the average field moderate through changes in the duty cycle.

Figure 2:
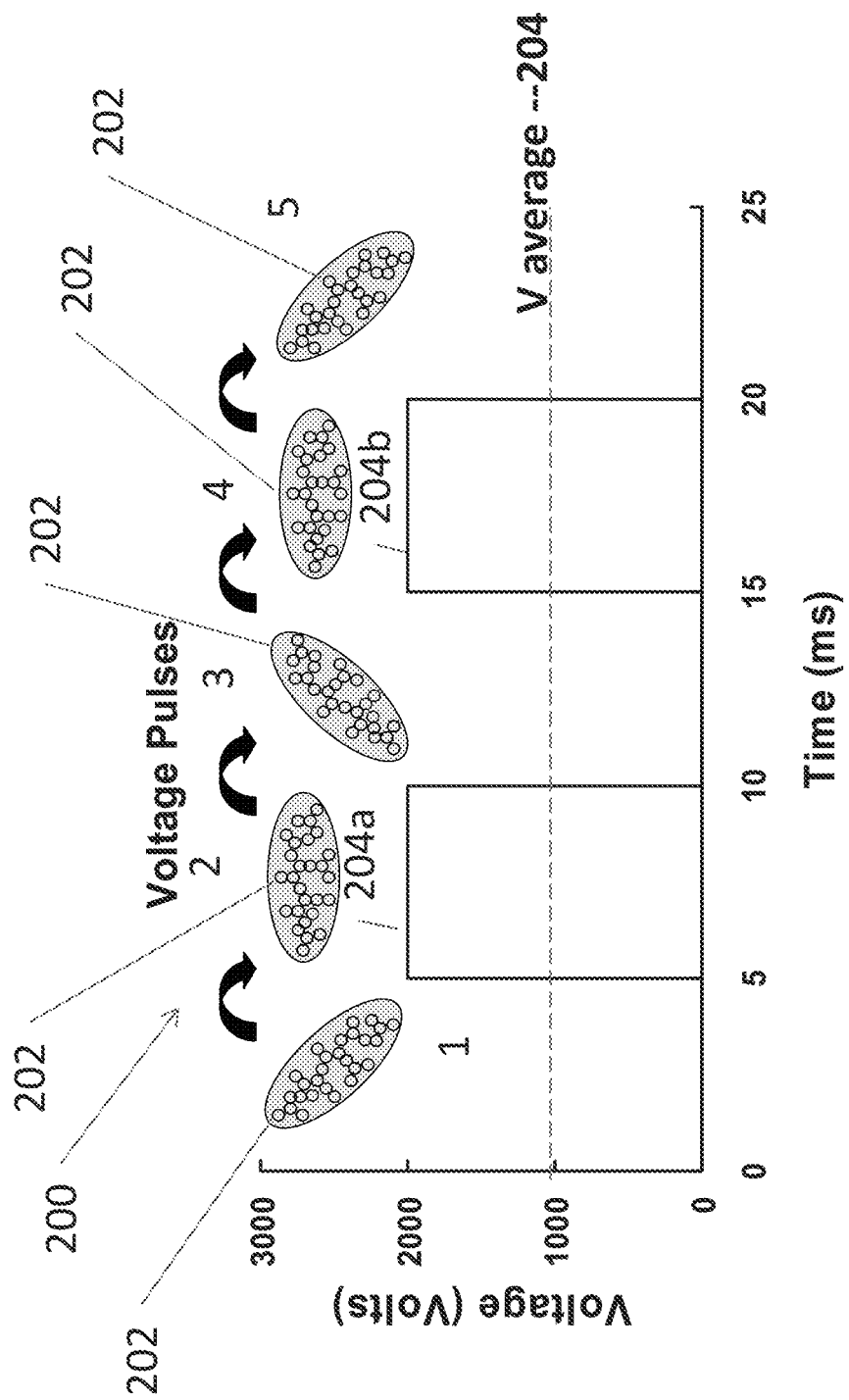
FIG. 2 is a schematic illustration according to embodiments of the present disclosure of an oscillating electric field to align particles (wires or aggregates). In this example, the pulse frequency is 100 Hz, the duty cycle is 50%, with a 2000 volt pulse. Thus the average voltage is 1000 V.

FIG. 2 illustrates an oscillating electric field 200 in the form of a square wave pulse 200a, 200b, . . . varying from zero to −V with a duty cycle equal to a fraction of the period. In the exemplary illustration of FIG. 2, the oscillating electric field 200 aligns a single particle (wire or aggregate) 202. In this example, the pulse frequency is 100 Hz, the duty cycle is 50%, with a 2000 volt pulse. Thus the average voltage V_average 204 is 1000 V. While the particle 202 is exposed to the high field, it will be partially aligned, and then returns to a random orientation when the field is removed. When the field is removed, there is no radial movement of the particle 202 in the DMA, so the effective movement in the radial direction only takes place when the particle is exposed to the high field. The change in the electrical mobility is measured as the alignment field intensity is changed. The electric field is determined by the voltage difference between the center and outer electrode and the gap distance between the electrodes as shown in FIGS. 5A, 5B1, 5B2, 5B3, 10A and 10B as further discussed below.

For a spherical particle the precipitation time from the inlet to the exit slit is only a function of the time averaged potential. Thus, if 1000 volts with a DMA sheath flow rate, $Q_{sh}$, corresponds to particles exiting the DMA at the peak in the inlet mobility distribution for spherical particles, then a pulsed field with a 25% duty cycle and a 4000 V at the DMA sheath flow rate, $Q_{sh}$, will also result in the peak mobility exiting the DMA.

Figure 3:
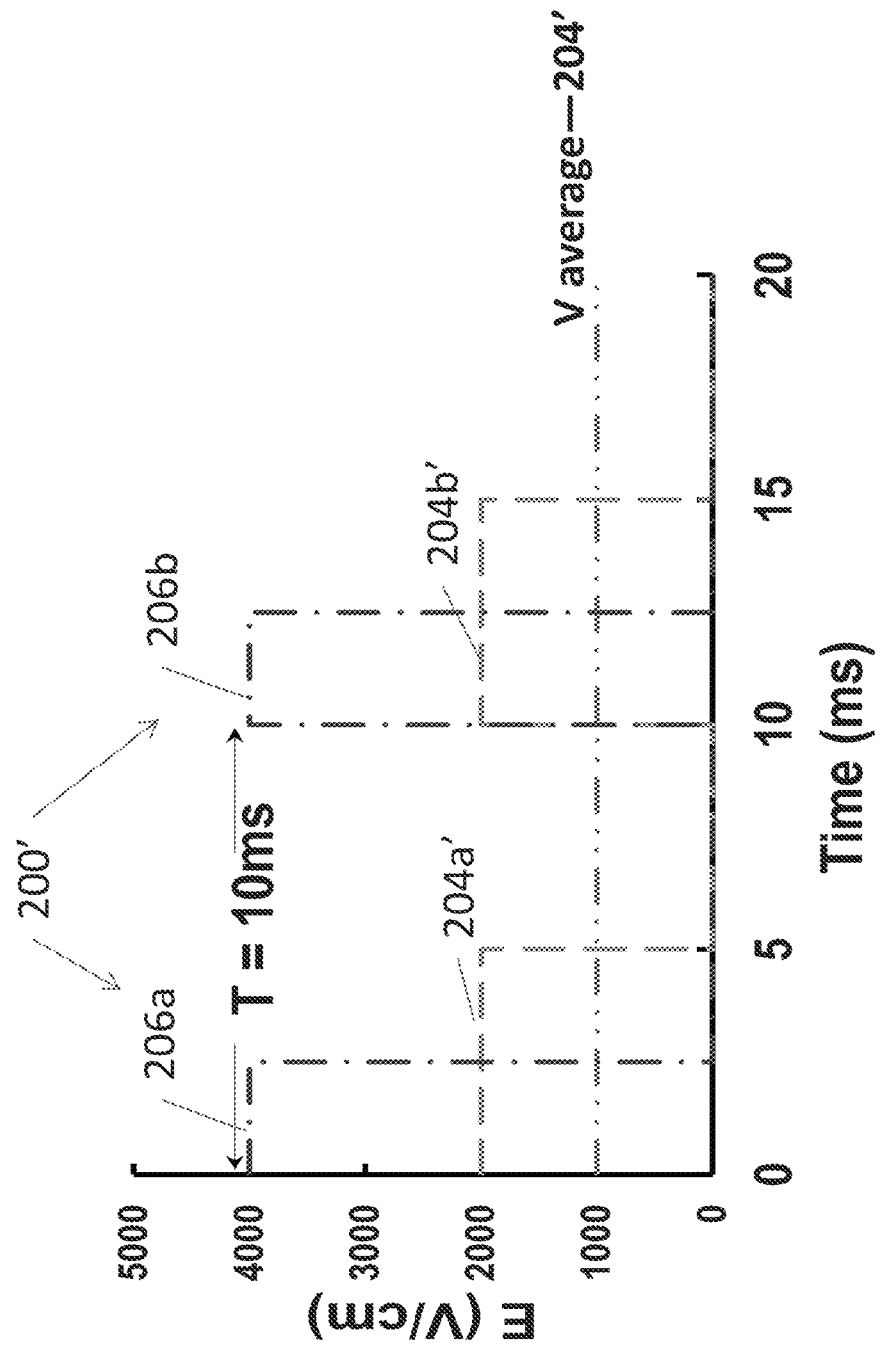
FIG. 3 is an illustration according to embodiments of the present disclosure of the relationship between the electric field and the pulse width to maintain a constant average field. Duty cycles vary from 100%, 50% to 25% with pulse frequency 100 Hz, and the corresponding fields are 1000, 2000 and 4000 V/cm respectively.

FIG. 3 illustrates the relationship between pulses 200' of the electric field E (in Volts/cm) and the pulse width T to maintain a constant average field V average—204' Duty cycles vary from 100% (at V average—204'), 50% (202a', 202b') to 25% (206a, 206b) with pulse frequency 100 Hz, and the corresponding fields are 1000, 2000 and 4000 V/cm respectively. Thus, FIG. 3 shows how one can vary the pulse field by about a factor of 2 (202a', 202b') or 4 (206a, 206b) while still keeping the average field V average—204 constant.

On the other hand, a non-spherical particle passing through the DMA will be partially aligned by the field so that the peak mobility will be shifted as the pulse width is decreased. During the period of alignment under high field, which is the effective time for particles traveling along the radial direction, the drag of the a non-spherical particle will be lower and thus its mobility higher than the equivalent sphere having mobility equal to that of the non-spherical particle uniformly averaged over all orientations. If the effect of the rise time of the pulse on the electrical mobility is negligible (see discussion in section 4 below), the pulsed field with a 25% duty cycle at sheath flow, $Q_{sh}$, is equivalent to a DC field at sheath flow, 4*$Q_{sh}$. Thus the mobility measured by a PFDMA is given by, $$Z_p = \frac{(Q_{sh}/D_{cycle})\ln(r_{out}/r_{in})}{2\pi V_e L_d}, \quad (6)$$

where $r_{in}$ is the radius of inner electrode of DMA, $r_{out}$ is the radius of outer electrode of DMA, $L_d$ is the 'active' length of DMA electrode, $Q_{sh}$ is the sheath flow rate, $D_{cycle}$ is the duty cycle of the pulse and $V_e$ is the DMA voltage. Theoretically, the transfer function and resolution of the PFDMA are the same as the DMA used in the PFDMA system. The ability to distinguish a rod however is determined by the extent to which the rod can be aligned, which is dependent on the field and aspect ratio.

The PFDMA is experimentally validated, i.e., calibrated, by comparing its measured results with the DMA (under DC voltage) with corresponding sheath flow rates as further described below with respect to FIGS. 5 and 10. The instrument is tested with Polystyrene latex (PSL) spheres with precisely known size, and gold rods, with dimensions determined by TEM. Both length and diameter of rods can be determined from the PFDMA measurements.

4. Experiments and Results

The PFDMA includes a pulser system connected with a DMA. The pulser system 400 illustrated in FIG. 4 generates square-wave high-voltage pulses. The output of this pulser system is then connected to a DMA for its voltage input. PFDMA is performed by the pulser system 400 signal 412 as input to a DMA, DMA2 422 IN FIGS. 5 and 10.

Different models of DMA can measure different range of particle size. Generally speaking, the PFDMA can apply to any model of DMA. In the present disclosure, the PFDMA is demonstrated and validated below using two commercially available models of DMA, however, the applications of PFDMA are not restricted to those particular DMA models.

4.1. Pulser System for PFDMA

Figure 4:
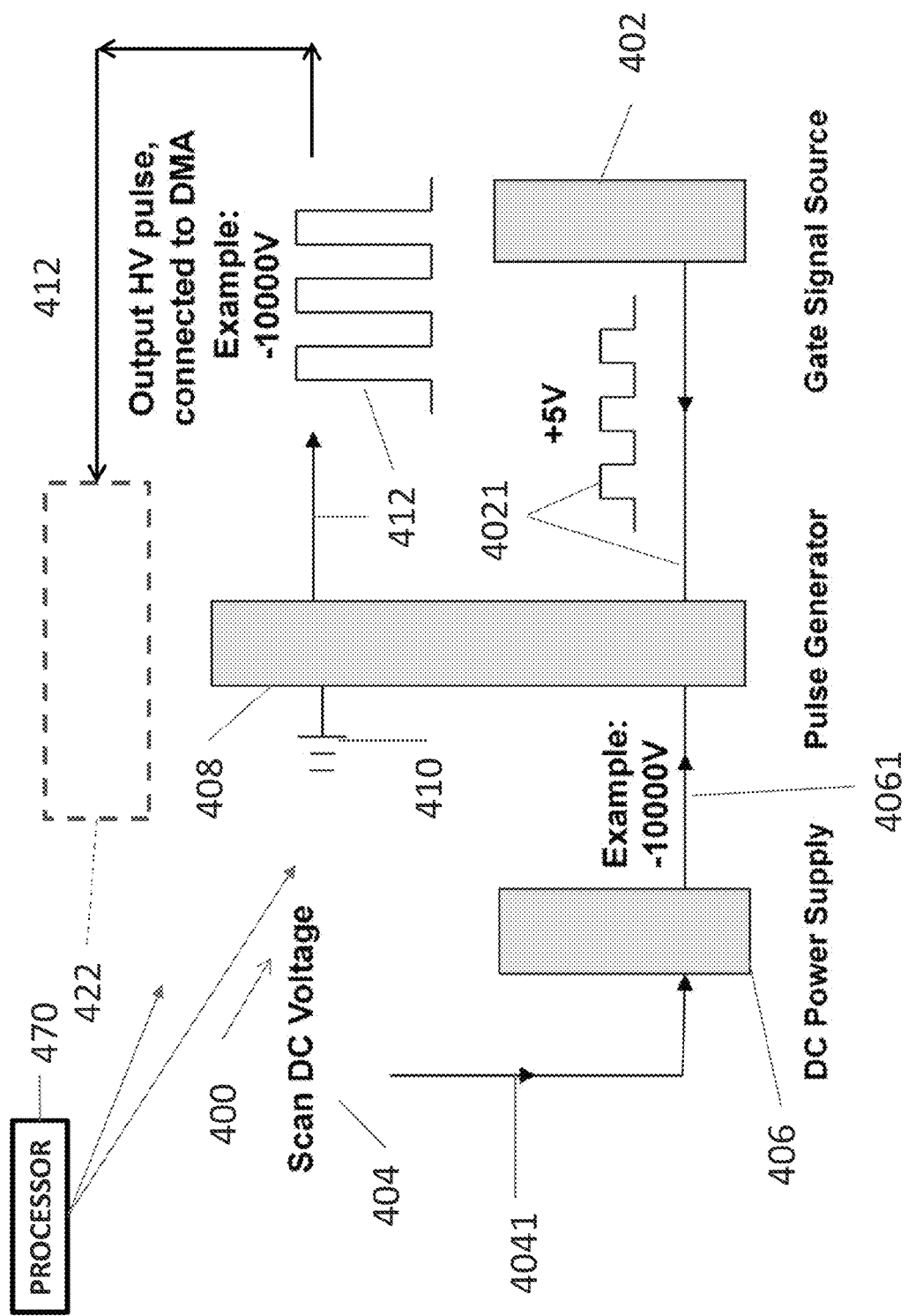
FIG. 4 is a schematic diagram according to embodiments of the present disclosure of a pulser system for generating square wave high voltage pulses to transmit to a pulsed field DMA (PFDMA) according to embodiments of the present disclosure.

FIG. 4 is a schematic diagram of a pulser system 400 for generating square wave high voltage pulses. The pulser system, which generates square-wave high-voltage pulses for the DMA's voltage input, has three components: a pulse generator, a gate signal source, and a DC power supply. The pulse generator has two inputs, one is connected to the gate signal source and another is connected to the DC power supply. The pulse generator has one output, which is also the output of the pulser system. This output provides high voltage pulses and is connected to a DMA for its voltage input. The duty cycle and frequency of the generated high voltage pulse are controlled by the gate signal source. And the height of the generated high voltage pulse is controlled by the DC voltage supply. When the voltage output of the DC voltage supply is changed, the height of the generated high voltage pulse is also changed accordingly.

Basically, a processor or computer 470 (with software) controls the voltage output of the DC power supply, thus in turn controls the height of the output pulse of the pulser system. It can increase the DC voltage output step by step. In each step, the DC voltage is a constant and one datuma point of particle concentration is measured at this voltage, which is related to a specific particle mobility size. Then the DC voltage is increased to a higher value for next datuma point measurement. After the concentrations of particles at various voltages are measured, by converting the voltages to corresponding particle mobility sizes, a concentration versus particle mobility size curve, i.e., a size distribution curve, will be obtained. by converting the voltages to corresponding particle mobility sizes Pulser system 400 generates square wave high voltage pulses which provide the basis for the extraction of particle geometric shape information from pulsed mobility measurements as described below in Section 4.3 and for the separation of particles based on the shape information as described below in Section 4.4. The pulser system 400 includes a function generator or gate signal source 402 that serves as a gate signal source outputting a square wave signal 4021 at a low voltage to pulse generator 408. Gate signal 4021 is the control signal which determines the shape of the pulses. The output of the gate signal is 0~5 volts. However, the output of the pulse generator 408 can reach 10000 or even higher depending on the design by the manufacturer.

The pulse generator 408 is in electrical communication with a ground 410 and is supplied electrical power from a high voltage DC power supply 406. "Scan DC voltage" 404 refers to the voltage output of the DC power supply controlled by a computer (with software) as described in above paragraph. The pulse generator 408 converts the input DC voltage 4061 to a square wave 412 of prescribed frequency and pulse width from gate signal source 402 The pulse generator 408 (e.g., IXYS Corp. DEI, PVX-4110, Fort Collins, Colo., USA) provides the required high voltage, rapid rise time, adjustable pulse width, and a clean square wave. The high voltage high frequency output 412 should be such that the output capacitance is less than about 200 pF (picofarads).

Although the pulser system 400 may be controlled manually by a user, processor 470 may be utilized to control the scanning of the DC voltage and also to control the general operation of the pulser system 400.

The performance of the PFDMA, the pulse generator 408 with the DMA2, 422, attached (as described below with respect to FIGS. 5, and 10 below), can be verified by monitoring the output 412 of the pulse generator 408 using an oscilloscope. In one exemplary experimental measurement, the generated pulse displayed at most a 60 ns rise and fall time, and an adjustable pulse width from 200 ns to DC. Consider that for a test rod-like particle, one similar to that evaluated in section 4.2 below (diameter=17 nm and length ~250 nm), the rotational relaxation time is about ~$10^{-5}$ s in the free molecular regime (Li et al. 2014). Thus both the rise time of the electronics and the particle rotational relaxation time are small compared to the pulse width (250 ms>width>0.5 ms for the long DMA and 50 ms>width>0.5 ms for the short DMA. The pulse widths applied is short relative to the transit time through the DMA (~860 ms for short DMA and ~8.3 s for long DMA).

FIG. 5 illustrates a tandem DMA and PFDMA measurement system 4000 that selects mono-dispersed particles and measures particle mobility at various electric fields according to embodiments of the present disclosure. Tandem DMA and PFDMA measurement system 4000 includes the pulser system 400 described above with respect to FIG. 4 to measure particle mobility at various electric fields.

A steady state poly-dispersed aerosol flow 4200 enters a bipolar charger or neutralizer 4211 to produce a known charge distribution. The neutralizer 4211 is in fluidic communication with the flow entry side of a DMA 421, designated as DMA 1, concurrently with sheath flow 4222. The poly-dispersed aerosol flow 4200 is exposed internally within DMA, 421 to a negative voltage -V1 from electrode 423 that is grounded via ground 424. The poly-dispersed aerosol flow concentration 4200 passes through DMA 1, 421 with a set sheath flow 4212 and aerosol flow 4200 and a set voltage to generate a mono-mobility aerosol 4210. The DMA 1, 421, is operated at a high flow rate ratio (more than 20) for the sheath flow 4222 to aerosol flow 4200 to improve the resolution in accurately measuring small changes in the mobility.

The sheath flow 4222 is exhausted (not shown) from DMA 1, 421, without mixing with the aerosol flow 4200 such that only mono-dispersed aerosol flow 4210 exits from DMA1, 421.

DMA and PFDMA measurement system 4000 further includes a pulsed field DMA system 450. Pulsed field DMA system 450 includes the pulser system 400 in electrical communication with an electrode 453 of a second DMA 452, designated as DMA 2. The electrode 453 is grounded via ground 454. The pulsed field DMA system 450 therefore includes the pulser system 400 and the second DMA 452, designated as DMA 2.

The mono-mobility aerosol 4210 exiting from DMA 1, 421, then passes through DMA 2, 452, wherein a pulse electric field is created in DMA 2, 452 via the pulser system 400. DMA 2, 452, is operated at a high flow rate ratio (more than 20) for the sheath flow 4522 to aerosol flow 4210 to improve the resolution in accurately measuring small changes in the mobility.

Processor 470 or processor 480 that controls the tandem DMA and PFDMA system 4000, either alone or in conjunction with processor 470, executes software to implement scanning as voltage steps the DC voltage from the DC power supply 406. A square wave electrical pulse 412 with rapid rise and fall, and small drop off is generated over the range of voltages of interest via the Pulser System 400.

The square wave 412 is generated at frequencies up to 500 Hz and at voltages up to 10,000 V via the pulser system 400. The frequency, pulse shape and duty cycle are defined via the signal generator or gate signal source 402 of the pulser system 400. The negative electrodes 423 and 453 each form a central rod, which is a metal, of the respective DMA 1, 421, and DMA 2, 452. Thus anywhere in the central rod is at the same negative voltage.

The mobility of the mono-disperse aerosol flow 4210 in DMA 2, 452, is measured as a function of the electric field by varying the duty cycle of the pulse occurring in DMA 2, 452. The mobility data is recorded via the processor 480 and the measured mobility data at various electric fields may be fit to the orientation-averaged mobility model described in Section 2 above, as one example of a suitable model, to obtain the shape information.

Thus, DMA2 in FIG. 5 is combined with the Pulser System 400 to become the PFDMA 450. It is the PFDMA 450 which extracts the particle shape information using the PFDMA. The PFDMA also performs the particle size separation based on the shape information as described below with respect to FIGS. 10, 10A and 10B.

Processor 480 executes the software for extracting the particle size information and also executes the software for separating the particles based on the shape.

Figure 5A:
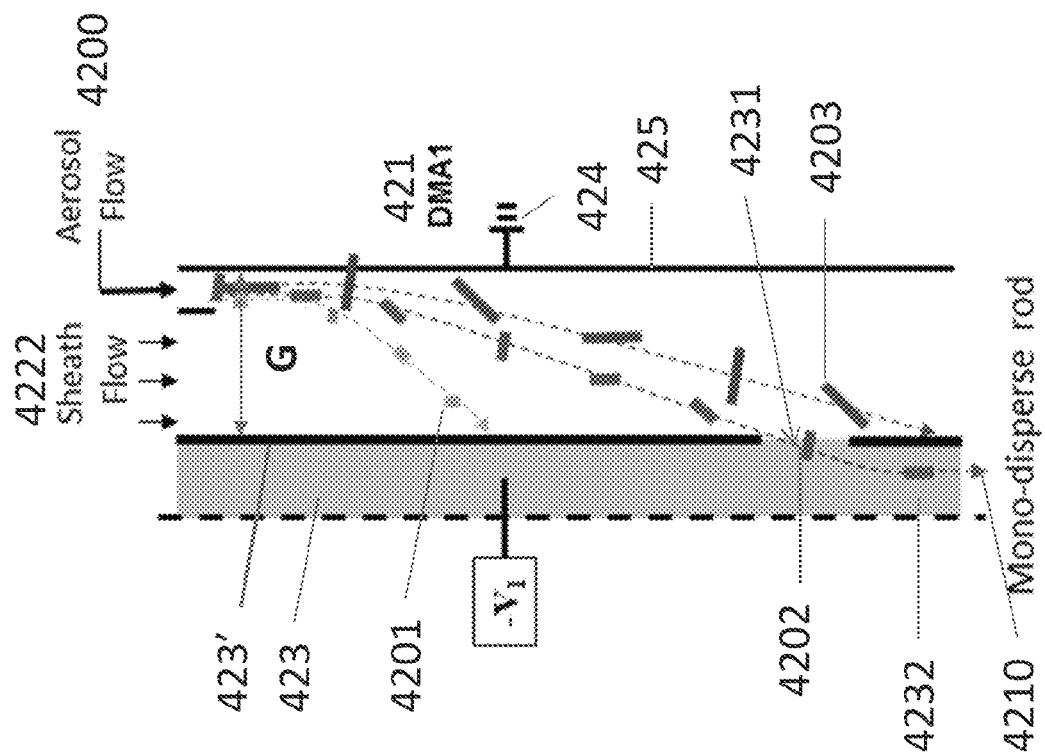
FIG. 5A is a schematic diagram according to embodiments of the present disclosure of the particle trajectories with similar shape entering a first DMA as a poly-diverse aerosol and exiting the first DMA as a mono-disperse aerosol.

FIG. 5A is a schematic diagram according to embodiments of the present disclosure of the particle trajectories with similar shape, e.g., first rod-like particles 4201, second rod-like particles 4202 and third rod-like particles 4203, entering DMA 1, 421, as poly-diverse aerosol concentration 4200 and exiting DMA 1, 421, as mono-disperse aerosol 4210 via an aperture 4231 defined in the central electrode 423 wherein the aperture 4231 enables fluid communication to a central flow path 4232 defined in the central electrode 423. Only this trajectory of particles 4202 is able to leave thru the monodisperse aerosol exit 4231. These particles are all charged. The aerosol flow enters only at the outer edge while the sheath fills all the cross section except the outer edge or wall 425.

In DMA 1, 421, the ground 424 and the negative voltage −V1 are shown to define the gap G of the Sheath Flow 4222. Gap G defines the gap for the sheath flow 4222 and also for the electric field (not shown) between the outer wall 425 of the DMA 1, 421 and the outer surface 423' of electrode 423. As the particles flow down thru the gap, they are driven by the electric field to the center electrode 423.

FIG. 5B1 is a schematic diagram according to embodiments of the present disclosure of the trajectories of particles with similar shape 4202 entering DMA 2, 452, at a low electric field at negative voltage $V_{2A}$ with respect to electrode 453 such that the particles 4202 remain randomly oriented with respect to the electric field in DMA 2, 452. The particles 4202 exit DMA 2, 452, via an aperture 4531 defined in the central electrode 453 wherein the aperture 4531 enables fluid communication to a central flow path 4532 defined in the central electrode 453.

FIG. 5B2 is a schematic diagram according to embodiments of the present disclosure of the trajectories of the particles with similar shape 4210 entering the DMA 2, 452 at an intermediate electric field at negative voltage $V_{2B}$ such that the particles 4202 become partially aligned with respect to the electric field in DMA 2, 453.

FIG. 5B3 is a schematic diagram according to embodiments of the present disclosure of the trajectories of the particles with similar shape 4202 entering the DMA 2, 452 at a high electric field at negative voltage $V_{2B}$ such that the particles 4202 become partially aligned with respect to the electric field in DMA 2, 453.

In one embodiment, mono-dispersed aerosol concentration flow 4200' (shown by the dashed lines) may be directly injected into DMA 2, 452, via bipolar charger or neutralizer 4211' to become mono-dispersed aerosol flow 4210' which then is acted upon by pulse field DMA system 450 in the same manner as described above with respect to the particles with similar shape 4210 entering the DMA 2, 452 in FIGS. 5B1, 5B2 and 5B3. Thus, DMA 1, 421, is bypassed or omitted in this mode of operation.

4.2. PFDMA Evaluation

The tandem DMA and PFDMA system 4000 was first evaluated using a mixture of two spherical singlet NIST traceable size PSL particles, of 127.1 nm (Thermo Scientific 3125A) and 200 nm (Thermo Scientific 3200A) to test the mobility distribution of two spherical particles at various frequencies. Next the PFDMA was evaluated using colloidal gold nanorods (Nanopartz Inc.; MUTAB coated conjugated gold nanorods; 10 nm, SPR=2000 nm, 0.25 mg, 1 mL; C12N-10-2000-TMU-0.25) to test the mobility of non-spherical particles, at various frequencies.

Validation of PFDMA Using Spherical Particles

The PFDMA system 450 of FIG. 5 is validated by measuring the mobility sizes of spherical particles, and comparing them with the results from a DMA that is a different DMA than DMA 1, 421, in FIG. 5.

Spherical PSL particles (PSL 127.1 nm and 200 nm spheres mixed in one sample) were aerosolized using a constant output pressure atomizer (TSI Inc., Shorewood, Minn., USA, Model 3076), and dried with two diffusion dryers before entering a neutralizer, which provides a bipolar charge distribution to the particles. The neutralized particles then pass through a long-DMA (TSI Inc. Model 3081) at DC voltage or a PFDMA for particle mobility size measurement and counted with an ultrafine Condensed Particle Counter (CPC) (TSI Inc. Model 3025A). The PFDMA (e.g., PFDMA system 450 in FIG. 5) for this part of the experiment is a long differential mobility analyzer column (TSI Inc. Model 3081) connected to high-voltage pulses generated with a pulser system described in FIG. 4. All ratios of the sheath flow rate to aerosol flow rate, e.g, sheath flow 4522 to aerosol flow 4210 in FIGS. 5B1, 5B2, 5B3, exceeded 20 to guarantee suitably high size resolution. To avoid the effects of time varying electric field as the particles go through the DMA, the DMA was operated in the step mode, and the step was maintained for a sufficiently long duration to ensure a complete transit through the DMA system before the voltage was changed (up to 45 seconds).

The DMA was calibrated by measuring the mobility of 100.7 nm NIST SRM particles and then adjusting the value of the flow in Eqn. (6) so that the measured mobility is equal to the mobility of a 100.7 nm SRM particle.

The mobility sizes of PSL 127.1 nm and 200 nm spheres were measured at DC voltages using a long-DMA at sheath flow rates $Q_{sh}$=3 l/min (0.5*10⁻⁴ m³/s) and $Q_{sh}$=12 l/min (2*10⁻⁴ m³/s). The same sample was also measured in a PFDMA with flow rates $Q_{sh}$=3 l/min (0.5*10⁻⁴ m³/s) and duty-cycle=25% (where $Q_{sh}/D_{cycle}$=12 l/min) at 1 Hz, 2 Hz, 5 Hz, 10 Hz, 50 Hz, 200 Hz and 500 Hz. The mobility size of this 127.1 nm PSL spheres was calibrated by 100.7 nm NIST standard reference material (PSL sphere) in a separate experiment. Then, the sheath flows were calibrated in all experiments by using the singlet peaks of 127.1 nm, i.e., obtaining the sheath flow rates and duty cycles by making the first singlet peaks showing exactly as 127.1 nm. Once the sheath flow of 3 l/min was calibrated, it was then fixed for all PFDMA measurements. The duty cycles were then calibrated in the PFDMA measurement by using the singlet peaks of 127.1 nm.

Figure 6:
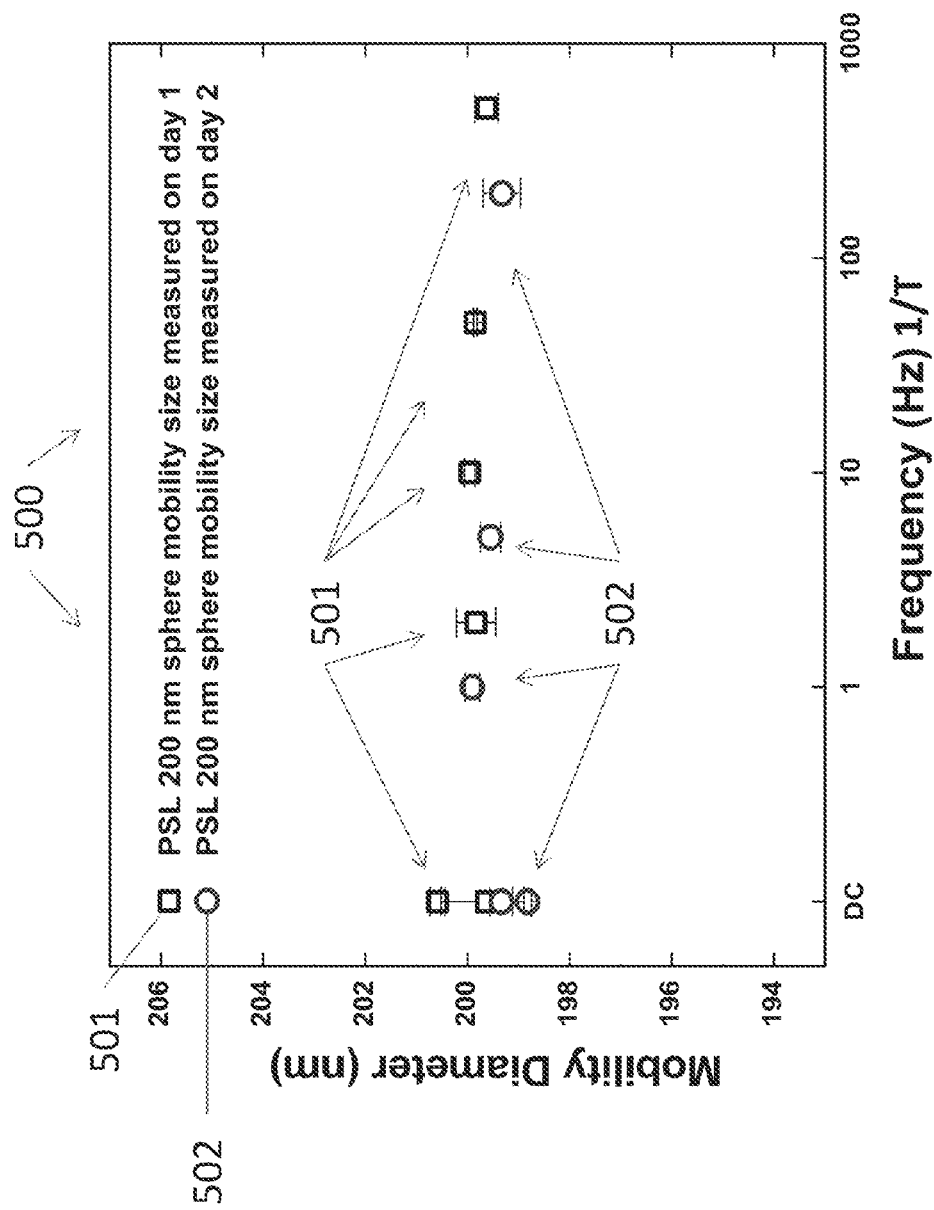
FIG. 6 is a graphical plot according to embodiments of the present disclosure of mobility diameter of 200 nm spheres measured at DC voltages using a long-DMA at sheath flow rates $Q_{sh}$=3 l/min (0.5*10$^{-4}$ m$^3$/s) and $Q_{sh}$=12 l/min (2*10$^{-4}$ m$^3$/s) wherein the same sample was also measured in a PFDMA with flow rates $Q_{sh}$=3 μmin (0.5*10$^{-4}$ m$^3$/s) and duty-cycle=25% at 1 Hz, 2 Hz, 5 Hz, 10 Hz, 50 Hz, 200 Hz and 500 Hz. The uncertainty bars were based on three repeat measurements.

Using this calibration, FIG. 6 is a plot 500 of mobility diameter $d_m$ in nanometers (nm) of 200 nm PSL spheres versus frequency (1/T) in Hertz (Hz). The mobility diameter $d_m$ is measured at DC voltages using a long-DMA at sheath flow rates $Q_{sh}$=3 l/min (0.5*10⁻⁴ m³/s) and $Q_{sh}$=12 l/min (2*10⁻⁴ m³/s). The same sample was also measured in a PFDMA with flow rates $Q_{sh}$=3 l/min (0.5*10⁻⁴ m³/s) and duty-cycle=25% at 1 Hz, 2 Hz, 5 Hz, 10 Hz, 50 Hz, 200 Hz and 500 Hz. The uncertainty bars were based on three repeat measurements.

The mobility sizes of the second singlet peaks (200 nm PSL) are shown for measurements 501 taken on Day 1 and measurements 502 taken on Day 2. The results show that the mobility of the sphere is independent of the frequency provided that the average field is constant. This validates the operation of the PFDMA. This is the theoretically expected result because the aerosol relaxation time is 10⁻⁷ s, which is a factor of 10⁴ less than the smallest pulse time used. This means that the sphere is accelerated to a constant velocity in a time negligible to the pulse time.

Validation of PFDMA Using Gold Nanorods

Next non-spheres, where alignment effects are expected, are considered and the PFDMA system 450 of FIG. 5 is compared with DMA 1, Gold nanorods, whose dimensions were determined by TEM experiments, diameter 17.1 nm and length 263 nm (with 4% uncertainty), were used for validating the performance of the PFDMA method for a non-sphere. The colloidal gold nanorod solution (Nanopartz Inc.; MUTAB coated conjugated gold nanorods; 10 nm, SPR=2000 nm, 0.25 mg, 1 mL; C12N-10-2000-TMU-0.25) was aerosolized using a 40-μm inner diameter capillary mounted in an electrospray aerosol generator (TSI Inc. Model 3480) with a neutralizer to provide a bipolar charge distribution to the particles. The neutralized particles were then passed through a short DMA (TSI Inc. Model 3085) and a PFDMA for particle mobility selection and counted with an ultrafine Condensed Particle Counter (CPC) (TSI Inc. Model 3025A). More details on the DMA measurement method can be found in Li el al. (2011a; 2011b) and Guha et al. (2012). The PFDMA system 450 here is a short differential mobility analyzer column (TSI Inc. Model 3085) (e.g., DMA 2, 452) connected to high-voltage pulses generated with a pulser system 400 described in FIG. 4.

The mobility size of the gold nanorods were measured under DC voltages (short DMA) at 3 l/min ($0.5*10^{-4}$ m$^3$/s), 6 l/min ($1*10^{-4}$ m$^3$/s) and 12 l/min ($2*10^{-4}$ m$^3$/s) sheath flow rates respectively; and under pulsed voltages (PFDMA) at 3 l/min ($0.5*10^{-4}$ m$^3$/s) sheath flow rate with a pulse duty cycle of 25% and 50% and frequencies of 5 Hz, 10 Hz, 100 Hz and 500 Hz, and at 6 l/min ($1*10^{-4}$ m$^3$/s) sheath flow rate with a pulse duty cycle of 50% and frequencies of 5 Hz, 10 Hz, 100 Hz and 500 Hz, respectively. The experimental conditions low, intermediate and, high electric fields are shown in FIG. 6-Table 1. All ratios of the sheath to aerosol flow exceeded 20 to guarantee suitably high size resolution. To avoid the effects of time varying electric field as the particles go through the DMA, the DMA was operated in the step mode, and the step was maintained for a sufficiently long duration to ensure a complete transit through the DMA system before the voltage was changed.

FIG. 7 Table 1 illustrates "Experimental conditions for gold nanorod mobility measurements." The electric field becomes higher as the $Q_{sh}/D_{cycle}$ becomes larger as shown in Eq. (6).

The mobility sizes of the gold nanorods were calibrated with 60 nm PSL spheres under the same experimental conditions. The mobility size of these 60 nm PSL spheres was calibrated by 100.7 nm NIST standard reference material (PSL sphere) in a separate measurement. The measurements with the standard reference material (100.7 nm), 60 nm PSL sphere and the gold nanorod were repeated three times respectively, and the assignment of DMA detection voltage was obtained by averaging the three means of the Gaussian fits to the experimental profile. The calibration procedures for gold rods using 60 nm PSL are as follows. The exact sheath flow value was assigned by measurement of the 60 nm PSL sphere at the same condition as the gold nanorod measurement under DC voltage. Once the sheath flow was calibrated, it was then fixed for all successive PFDMA measurements. The duty cycle was then calibrated in the PFDMA measurement using the 60 nm PSL. Using this calibrated sheath flow value and the duty cycle, the mobility sizes of the gold rod could be determined by Eqn. (6). Uncertainty bars for mobility sizes are based on three repeat voltage scans.

Figure 8:
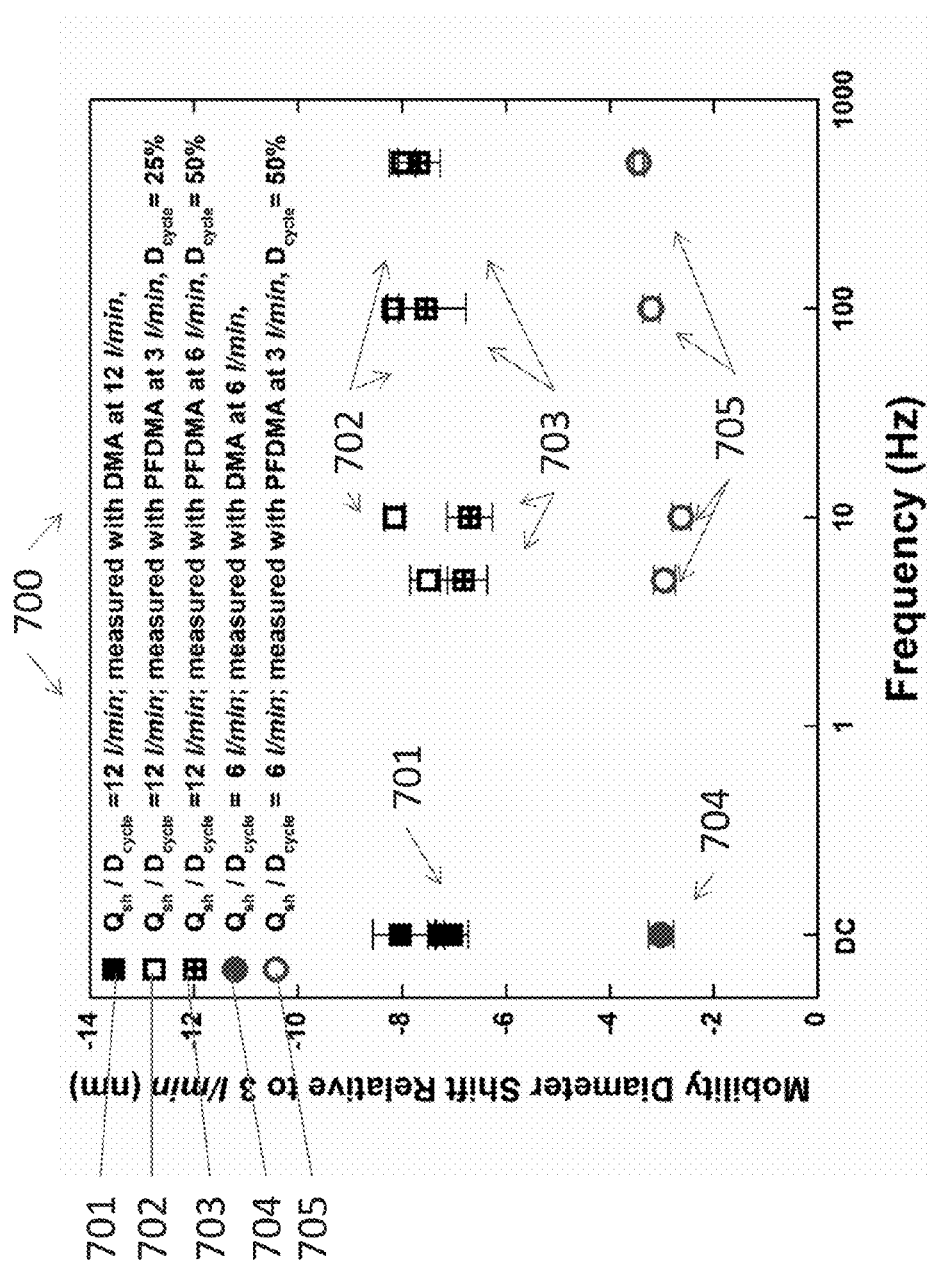
FIG. 8 is a graphical plot according to embodiments of the present disclosure of the mobility size shift of gold nanorod (17 nm*270 nm) with respect to the low DC voltage 3 l/min (0.5*10$^{-4}$ m$^3$/s) case ($d_m$~73 nm) versus pulse frequency wherein the zero frequency condition is the DC voltage case.

FIG. 8 is a plot 700 of mobility size shift of gold nanorod (17 nm*270 nm) with respect to the low DC voltage 3 l/min ($0.5*10^{-4}$ m$^3$/s) case ($d_m$~73 nm) versus pulse frequency. The zero frequency condition is the DC voltage case. The mobility sizes measured between a DC voltage short DMA and a PFDMA with the same flow rate to duty cycle ratio are consistent among all experiments. There is no apparent frequency dependency among all measured frequencies. The uncertainty bars were based on three repeat measurements.

The mobility size shift of gold nanorods were measured by a PFDMA (e.g., PFDMA system 450 in FIG. 5), and a DMA in high ($Q_{sh}/D_{cycle}$=12 l/min) and intermediate electric field ($Q_{sh}/D_{cycle}$=6 l/min). The results are presented as a mobility diameter shift (on Y-Axis) as relative to the low electric field (DC voltage, 3 l/min) case ($d_m$~73 nm) as a function of pulse frequency in Hz. The detailed experimental conditions are shown in FIG. 7-Table 1:

In FIG. 8, Low electric field 700' is the reference line (y=0) in FIG. 7. The shift values between the values of all other data and the value at this Low Electric Field. are shown as follows:

Plot 701 represents $Q_{sh}/D_{cycle}$=12/min, measured with DMA at 12 l/min.

Plot 702 represents $Q_{sh}/D_{cycle}$=12/min, measured with DMA at 3 l/min, $D_{cycle}$=25%.

Plot 703 represents $Q_{sh}/D_{cycle}$=12/min, measured with DMA at 6 l/min, $D_{cycle}$=50%.

Plot 704 represents $Q_{sh}/D_{cycle}$=6/min, measured with DMA at 6 l/min.

Plot 705 represents $Q_{sh}/D_{cycle}$=6/min, measured with DMA at 3 l/min, $D_{cycle}$=50%.

First the measured mobility sizes for gold nanorods (non-spherical particle) are consistent between a DMA and the PFDMA with the same flow rate to duty cycle ratio ($Q_{sh}/D_{cycle}$) which defines the intensity of the electric field. The mobility size shift, is ~8 nm, at high ($Q_{sh}/D_{cycle}$=12 μmin) and ~3 nm, at intermediate field ($Q_{sh}/D_{cycle}$=6 l/min) for both PFDMA and DMA measurement, with no discernible frequency dependency with this normalization.

These results clearly show that the PFDMA when used on both spherical and rod like particles behaves as expected. The PFDMA enables one to change the peak E-field experienced by the particle without changing the flow, thus can be used to measure the mobility of a non-spherical particle at various electric fields which opens up the opportunity to an eventual shape evaluation as will be discussed in the next section (section 4.3), and to particle separation based on shape as will be discussed in the section 4.4.

Figure 9:
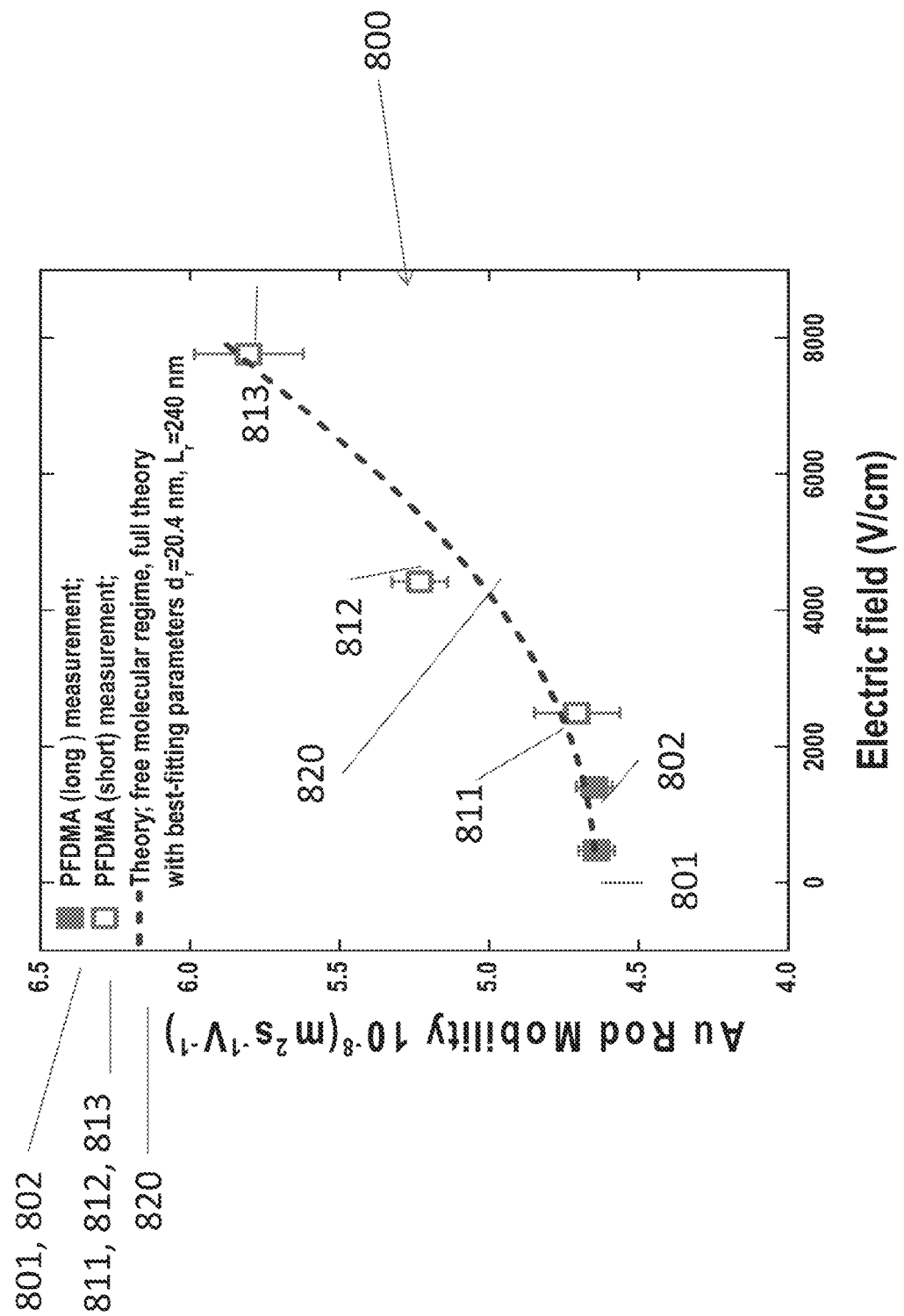
FIG. 9 is a graphical plot according to embodiments of the present disclosure of experimental measured mobility for gold rods at various applied fields, where the dimensions of the gold rods were determined by TEM as diameter $d_r$=17.1 nm and length $L_r$=263 nm.

There are two applications (or modes of operation) of PFDMA system 4000. One is extracting particle geometric shape information from pulsed mobility measurements, and the other is separating particle based on their shapes using PFDMA. Both applications can use the same setup as shown in FIG. 9. If the particles are poly-dispersed, a DMA as DMA1 in FIG. 9 is necessary to size-select particles and make the particle monodispersed, then a PFDMA applies for the application of "extracting particle geometric shape information". However, if the particles are monodispersed, there is no need for a DMA as DMA 1 in FIG. 9 to pre-select the particles for this application. A sole PFDMA is adequate to extracting particle shape information as demonstrated in Section 4.3 where Au-nanorods are monodispersed.

4.3. Extracting Particle Geometric Shape Information from Pulsed Mobility Measurements One application of PFDMA is extracting particle geometric shape information from pulsed mobility measurements.

Since the Au-nanorods are monodispersed, FIG. 5 illustrates a Direct injection of Mono-dispersed Aerosol Flow into a PFDMA 450 that measures particle mobility at various electric fields according to embodiments of the present disclosure.

In this section, a least-squares fitting procedure is demonstrated that can be employed to extract the dimensions (diameter and length) of gold nanorods by measuring the mobility shift at various peak electric fields and the use of the model Eqns. (2), (3) (4) and (5).

FIG. 9 is a plot 800 showing the experimentally determined mobility of gold rods, Au Rod Mobility $10^8$ (m$^2$s$^{-1}$V$^{-1}$) on the Y-axis, using the PFDMA as a function of the applied electric field in a wide range, from low to high, Electric field (V/cm) on the X-axis.

More particularly, mobility for gold rods at various applied fields were experimentally measured, where the dimensions of the gold rods were determined by TEM as diameter $d_r$=17.1 nm and length $L_r$=263 nm. Blue dotted line: full theory for rod with nonlinear least-squares best-fitting parameters, $d_r$=20.4±0.8 nm and $L_r$=240±25 nm.

In this analysis, mobility is regarded as a constant corresponding to an electric field equal to the electrode voltage divided by the radial distance between the two electrodes. The calculation shows that the radial variation in the electric field affects the value of the mobility by less than 0.7%. The mobility at three high electric fields 811, 812, 813 were measured by a PFDMA with short DMA column, and the mobility at two low electric fields 801, 812 were measured with a long column PFDMA. As expected higher fields result in more alignment and thus higher mobility. The accurate dimensions of the monodisperse gold rods were determined by TEM (the averaged diameter and length of 38 mobility selected rods at peak voltage is $d_r$=17.1 nm and length $L_r$=263 nm; with 4% uncertainty).

Once the data are measured using a PFDMA, for the application to 'extraction of particle shape information', for example to obtain the length and diameter of a gold rod, a data analysis algorithm based on our particle mobility theory is still needed. A least-squares fitting procedure was demonstrated below to extract diameter and length of the gold rods by use of our model and the experimental data measured by a PFDMA in FIG. 8.

Using the theory represented by Eqn. (2), both the diameter and length of the rods can be extracted directly from the experimental measured mobility in FIG. 8. The actual implementation of a nonlinear least square fit to Eqn. (2) was greatly simplified using the slender rod approximation for the values of polarizability, i.e., Eqn. (5). A nonlinear least-squares computer procedure (Wolfram Mathematica 8.0; FindFit ( ) for 5<$d_r$<50, 5<$L_r/d_r$<50) was used to fit Eqn. (2) with the $K_\perp$ and $K_\square$ given in Eqns. (3-1, 3-2) and the ($\cos^2\theta$) given in Eqns. (4, 5) to the mobility data in FIG. 9. From this curve fitting procedure, best values of the two parameters, $d_r$ and $L_r$ were obtained as $d_r$=20.4±0.8 nm and $L_r$=240±25 nm, which is consistent with the TEM measured rod dimensions, of $d_r$=17.1 nm and $L_r$=263 nm. The rod diameter of the fitting result is off by ~16% compared with the TEM analysis, while the rod length is underestimated by ~9%. Possible reasons for this discrepancy are the day-to-day DMA measurement variation, the accuracy of the free molecular expression for this size of gold rod, and the uncertainties of the TEM analysis. Unfortunately a small uncertainty in mobility is magnified when converted to the nanorod dimension. The best fitting parameters obtained in this work are based on measurements over five days.

The theoretical curve using the full theory with best-fitting parameters, $d_r$=20.4 nm and $L_r$=240 nm, is shown as the blue dotted curve 820. The slender rod approximation based on Eqn. (5) (which is not shown in the figure) is very close to the full theory and the two theoretical curves are basically overlapped with each other (the maximum deviation of the mobility within the plot range between the two theories is 0.23%).

4.4. The Potential of PFDMA for Particle Separation Based on their Shapes

The second application is separating particles based on shape. The effect of particle alignment under electric field, which when implemented with the simplicity of the PFDMA, can be used to separate particles based on their shapes. Two different shape particles having the same mobility size under at one value of electric field, would show a different mobility size under a different field strength. The evaluation of this approach employs a DMA in series with a PFDMA as shown in FIG. 10.

FIG. 10 illustrates a measurement system with the first DMA used to select mono-mobility particles and the pulsed field DMA (PFDMA) to separate spheres from nanowires. Clean and filtered sheath flow enters the DMA at the top with sheath flow rate, $Q_s$. Aerosol particles (spheres and rods in above figure) enter DMA at the outside column with aerosol flow rate, $Q_a$, and exit the DMA through the slit located at the central rod. The trajectory of aerosol particles through DMA is shown in above figure using a simplified straight line. These exiting aerosol particles with selected mobility from the first DMA will pass through the second PFDMA for particle separation, and the exiting aerosol particles from the second PFDMA which are separated based their shape will be counted by the CPC.

More particularly, FIG. 10 illustrates the tandem DMA-PFDMA measurement system 4000 of FIG. 5 that includes the pulser system 400 described above with respect to FIG. 4 but now configured and disposed to extract particle shape information and separate particles based on their shape. Accordingly, the tandem DMA-PFDMA measurement system of FIG. 10 is designated as tandem DMA-PFDMA measurement system 4000' since it is generally the same as tandem DMA-PFDMA measurement system 4000 except that aerosol particles with different shapes (spheres and rods) pass through tandem DMA-PFDMA measurement system 4000'.

More particularly, tandem DMA-PFDMA measurement system 4000' again includes first DMA1, 421, that is configured and disposed to select mono-mobility particles 430 and a PFDMA, that is configured and disposed to separate spheres 440 from nanowires 450. Particle 420 enters the first DMA1, 421, through a charge neutralizer 4211. Sheath flow 4222' also enters the first DMA1, 421, so as to enable the first DMA1, 421, via a DC voltage, to select the mono-mobility particles 4260. The mono-mobility particles 4260 exit the DMA1, 421, as an aerosol flow stream that enters DMA 2, 452 of PFDMA system 450'. Sheath flow 4522' enters DMA 2, 452, so as to enable the second DMA2, 452, to separate spheres 4400 from nanowires 4500. The separated particles spheres 4400 and nanowires 4500 may be counted via charged particle counter 4600. Again, the sheath flows 4222' and 4522' are exhausted (not shown) from DMA 1, 421 and DMA 2, 452, without mixing with the aerosol flows 4250 and 4260.

Conceptually if there is a polydisperse distribution of spheres and nanrods entering the first DMA1 421, which is operating at a low enough field that the particle's orientation is nearly random, then exiting the first DMA1 421 is a mixture of nanowires with fixed length and diameter, (nanowires at inlet assumed to have the same diameter), and a fixed diameter of spheres. The alignment effect caused by the second DMA2 452 operating in a pulsed mode results in the separation of the nanowires at a lower detection voltage than the spheres.

The voltage is scanned in a range for obtaining a size distribution. The voltage is not a fixed value. For example in DMA2, the spheres are collected in V2*a*, the rods will be collected in V2*b*.

Figures 10A, 10B:
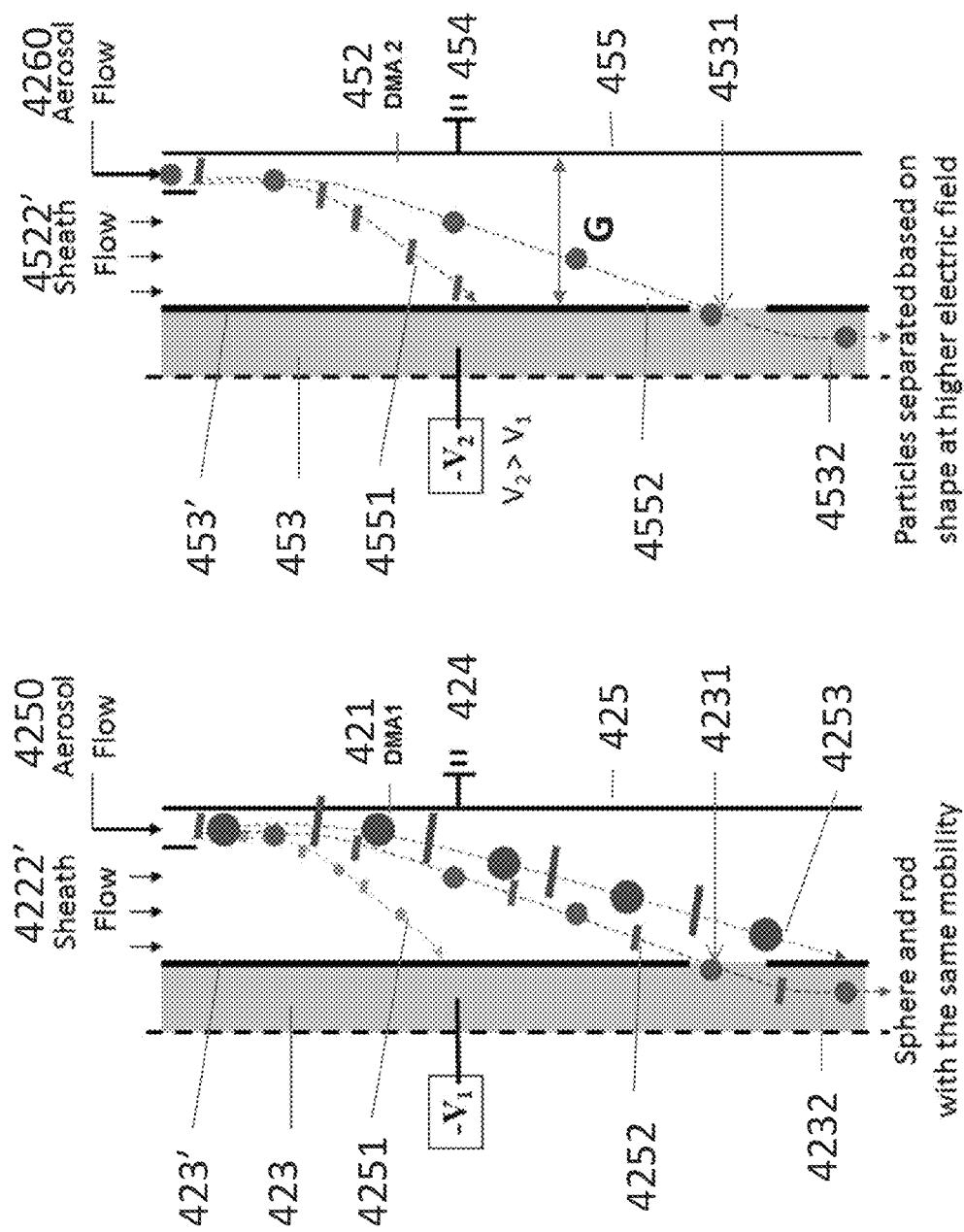
FIG. 10A is a schematic diagram according to embodiments of the present disclosure of the particle trajectories (sphere and rod) internal to the DMA of the tandem DMA and pulse field differential mobility analyzer system of FIG. 10 illustrating mono-mobility particle selection with mixed spheres and rods.
FIG. 10B is a schematic diagram according to embodiments of the present disclosure of the particle trajectories (sphere and rod) internal to the pulse field differential mobility analyzer of the pulse field differential mobility analyzer system of FIG. 10 illustrating separation of the particles based on their shape.

FIG. 10A illustrates the particle trajectories of mono-mobility spheres and rods internal to DMA 1, 421 of the tandem DMA and pulse field differential mobility analyzer system 4000' of FIG. 10. More particularly, particle trajectory 4251 illustrates a first trajectory of spheres and rods having the same mobility, particle trajectory 4252 illustrates a second trajectory of spheres and rods having the same mobility, and particle trajectory 4253 illustrates a third trajectory of spheres and rods having the same mobility, Based on their mobility, particles in the second trajectory 4252 exit DMA 1, 421, as aerosol concentration 4260 via aperture 4231 defined in the central electrode 423 wherein again the aperture 4231 enables fluid communication to central flow path 4232 defined in the central electrode 423. Only this trajectory of particles 4252 is able to leave thru the mono-mobility aerosol exit 4231. These particles are all charged. The aerosol flow enters only at the outer edge while the sheath fills all the cross section except the outer edge or wall 425.

FIG. 10B illustrates the particle trajectory 4551 of rods and the particle trajectory 4552 of spheres both internal to DMA 2, 452 the rods in particle trajectory 4551 are separated from the spheres in particle trajectory 4552 based on their shape due to the application within DMA 2, 452, of a pulse negative voltage −V2 that is greater than the voltage −V1 that has been applied within DMA 1, 421.

In a similar manner as described above with respect to FIG. 10A, the spherical particles in the second trajectory 4552 exit DMA 2, 452, as aerosol concentration 4260 via aperture 4531 defined in the central electrode 453 wherein again the aperture 4531 enables fluid communication to central flow path 4532 defined in the central electrode 453. Only this trajectory of particles 4552 is able to leave thru the mono-mobility aerosol exit 4531. These particles are all charged. The aerosol flow enters only at the outer edge while the sheath fills all the cross section except the outer edge or wall 455.

The particles in trajectory 4552 may be separated into aerosol 4400 as spheres or if the particles in trajectory 4552 are instead rods or nanowires, they may be separated into aerosol 4500. The particles may be counted via particle counter CPC 4600.

With an initial barrier between the sheath flow and the aerosol flow, the sheath flow 4222' remains as laminar flow and is exhausted (not shown) from DMA 1, 421, without mixing with the aerosol flow 4250 such that only mono-dispersed aerosol flow 4260 exits from DMA1, 421. Similarly, the sheath flow 4522' remains as laminar flow and is exhausted (not shown) from DMA 2, 452 without mixing with the aerosol flow 4260.

Figure 11:
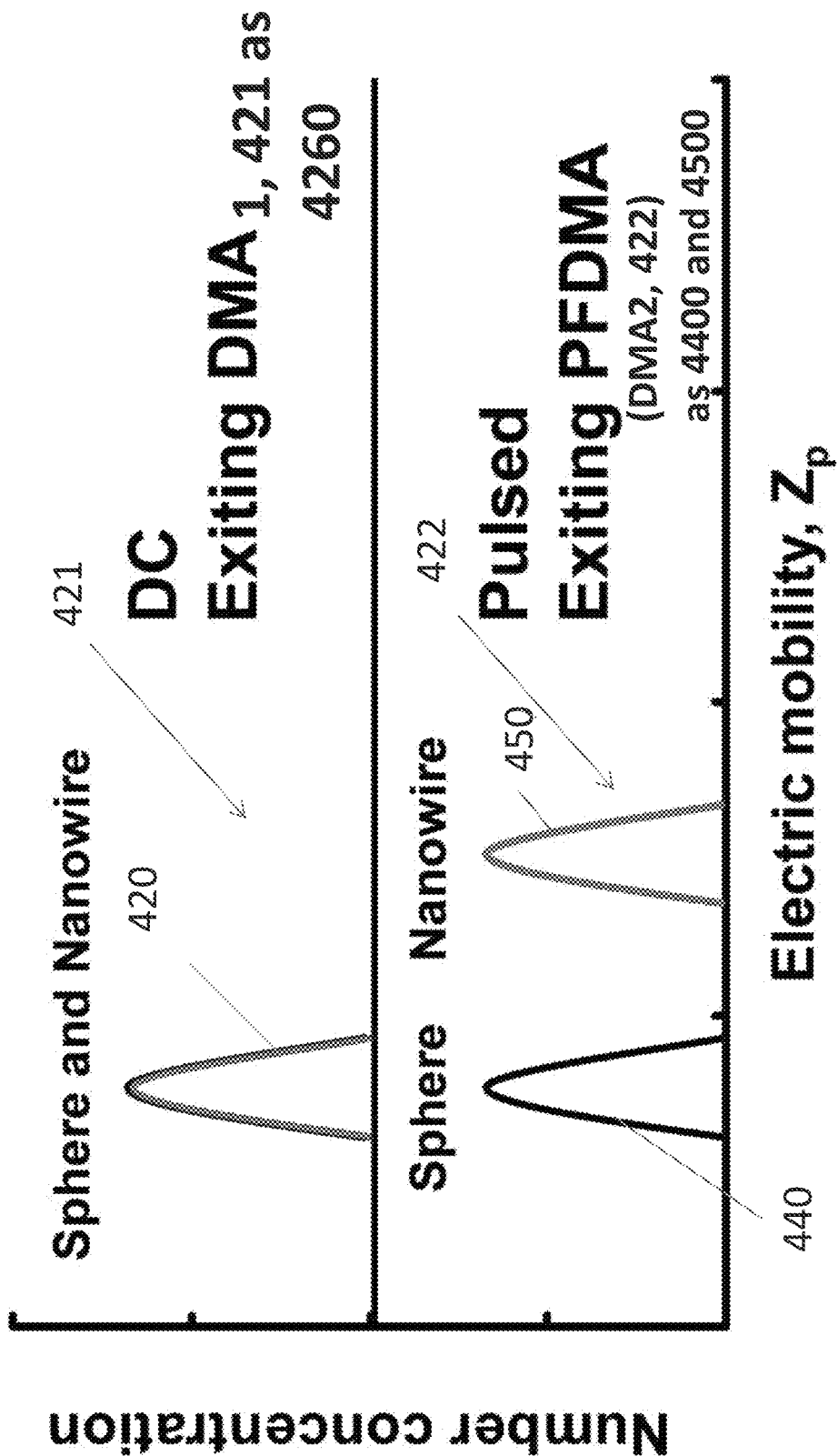
FIG. 11 is a schematic illustration of the mobility distribution of particles exiting the tandem DMA-PFDMA system of FIGS. 10, 10A and 10B.

FIG. 11 illustrates schematically the mobility distributions of the particles exiting the first DMA1, 421, and second DMA2, 452. The Y-axis indicates schematically the number concentration. The X-axis indicates schematically the electric mobility, Z. The particles 4250 are first measured by a DC voltage in the first DMA1, 421, and exit the first DMA1, 421, as the mono-mobility particles 4260. The mono-mobility particles 4260 enter the second DMA2, 452, and exit the PFDMA (pulsed DC DMA2, 452), separately as spheres 4400 and nanowires 4500.

Figure 12:
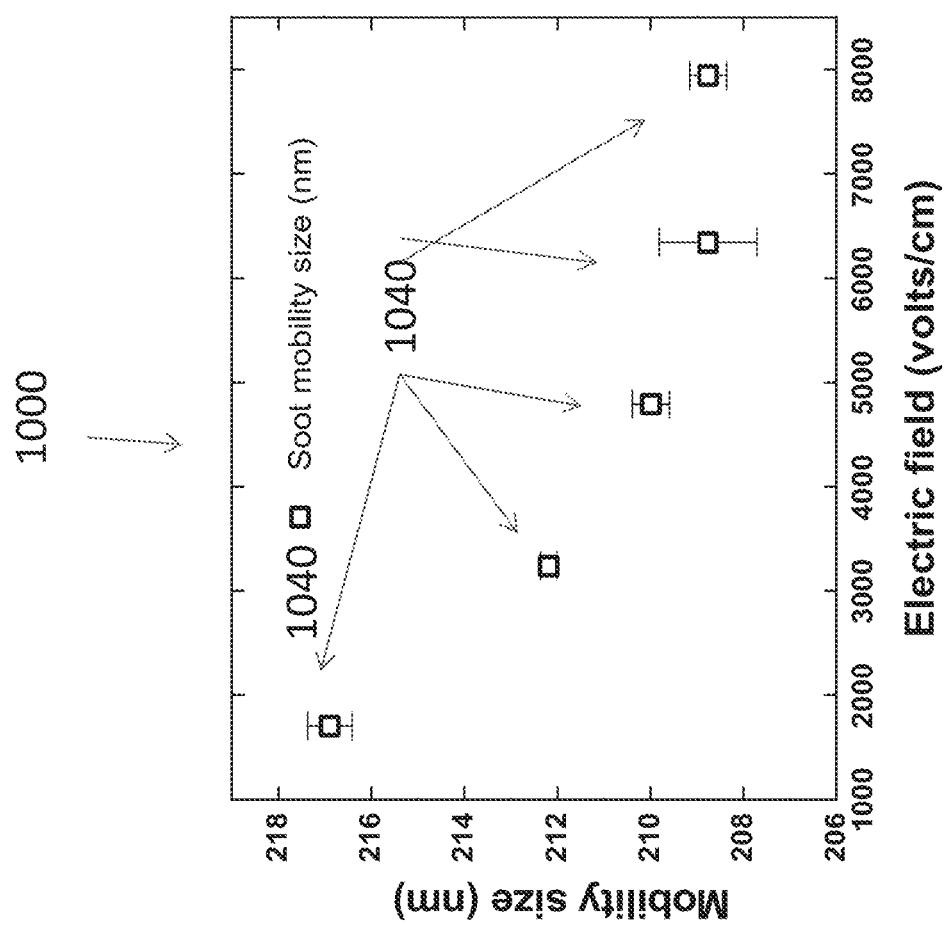
FIG. 12 is a schematic illustration according to embodiments of the present disclosure of the mobility size of soot aggregates as a function of Electric field measured by the tandem DMA and PFDMA system of FIGS. 10, 10A and 10B.

FIG. 12 illustrates the mobility size of soot aggregates as a function of Electric field measured by PFDMA. The soot was generated from combustion and is a combustion product. The graphical plot 1000 illustrates a variation of the mobility size in nm of the non-spherical aggregates 1040 plotted on the Y-axis versus the electric field in volts/cm plotted on the X-axis. Since the mobility size of spherical particles is a constant, the above experimental result shows that the tandem DMA and PFDMA system 4000' could be used to separate non-spherical aggregates 4500 from spherical particles 4400. Only aggregates and no spheres were tested.

Description of Method

Figure 13B:
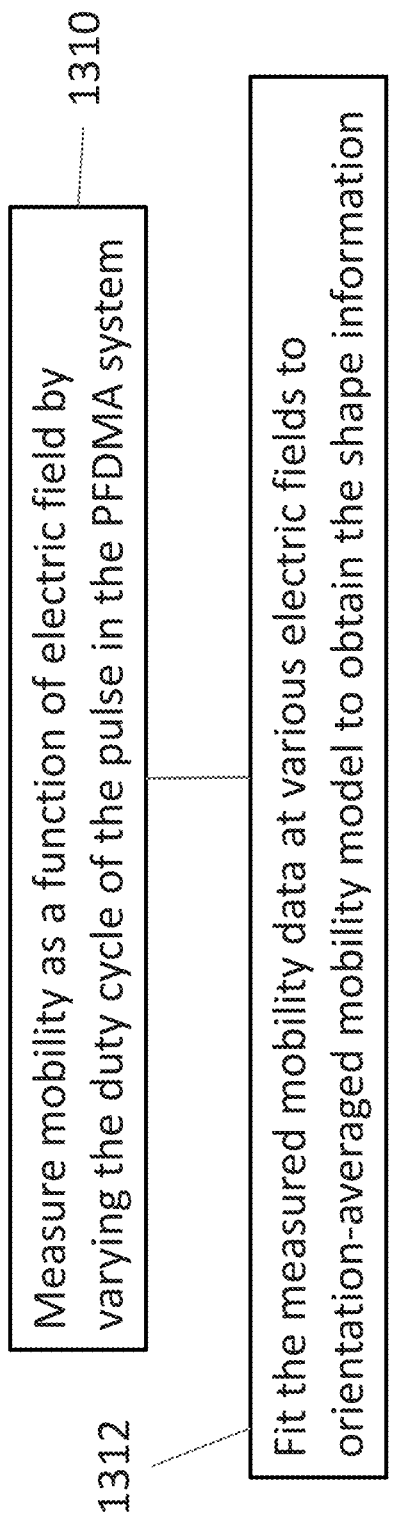
FIG. 13B is continuation of the block diagram of FIG. 13A.

FIGS. 13A and 13B are block diagrams of the method according to embodiments of the present disclosure of general steps 1300 of applying the tandem DMA and PFDMA system of FIGS. 5, 5A and 5B1, 5B2, 5B3 to particles of similar shape to extract shape information.

Following START 1301 for particles with similar shape to apply tandem DMA-PFDMA system to "extract shape information", step 1302 includes generating a steady state aerosol concentration. Step 1304 includes passing an aerosol flow from the aerosol concentration thru a bipolar charger (neutralizer) to produce a known charge distribution.

Step 1306 includes passing the aerosol thru a DMA with set sheath and aerosol flows and a set voltage to generate a mono-mobility aerosol.

Step 1308 includes passing the mono-mobility aerosol thru a PFDMA system.

Step 1310 includes measuring mobility as a function of electric field by varying the duty cycle of the pulse in the PFDMA system.

Step 1312 includes fitting the measured mobility data at various electric fields to orientation-averaged mobility model to obtain the shape information.

Figure 14B:
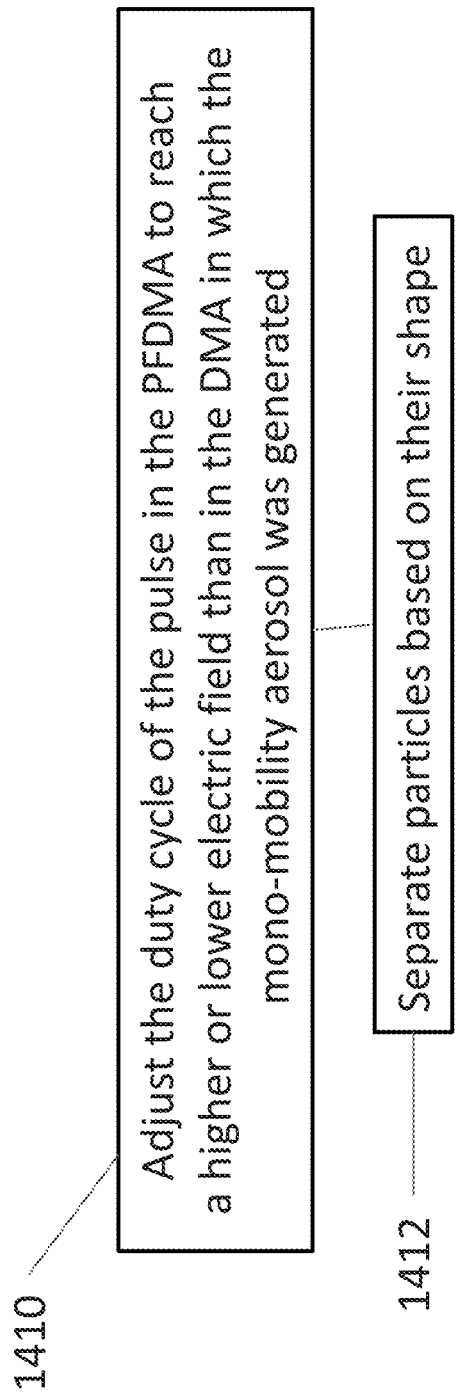
FIG. 14B is continuation of the block diagram of FIG. 13A.

FIGS. 14A and 14B are block diagrams of a method 1400 according to embodiments of the present disclosure of general steps of applying the tandem DMA and PFDMA system of FIGS. 10, 10A and 10B to particles of different shapes to separate particles based on their shape.

Following START 1401 for particles with different shapes, applying tandem DMA-PFDMA to "separate particles based on their shape", step 1402 includes generating a steady state aerosol concentration.

Step 1404 includes passing an aerosol flow from the aerosol concentration with different shapes through a bipolar charger (neutralizer) to produce a known charge distribution.

Step 1406 includes passing the aerosol thru DMA with set sheath and aerosol flows and a set voltage to generate a mono-mobility aerosol.

Step 1408 includes passing the mono-mobility aerosol thru the PFDMA.

Step 1410 includes adjusting the duty cycle of the pulse in the PFDMA to reach a higher or lower electric field than in the DMA in which the mono-mobility aerosol was generated.

Step 1412 includes separating particles based on their shape.

Figure 15B:
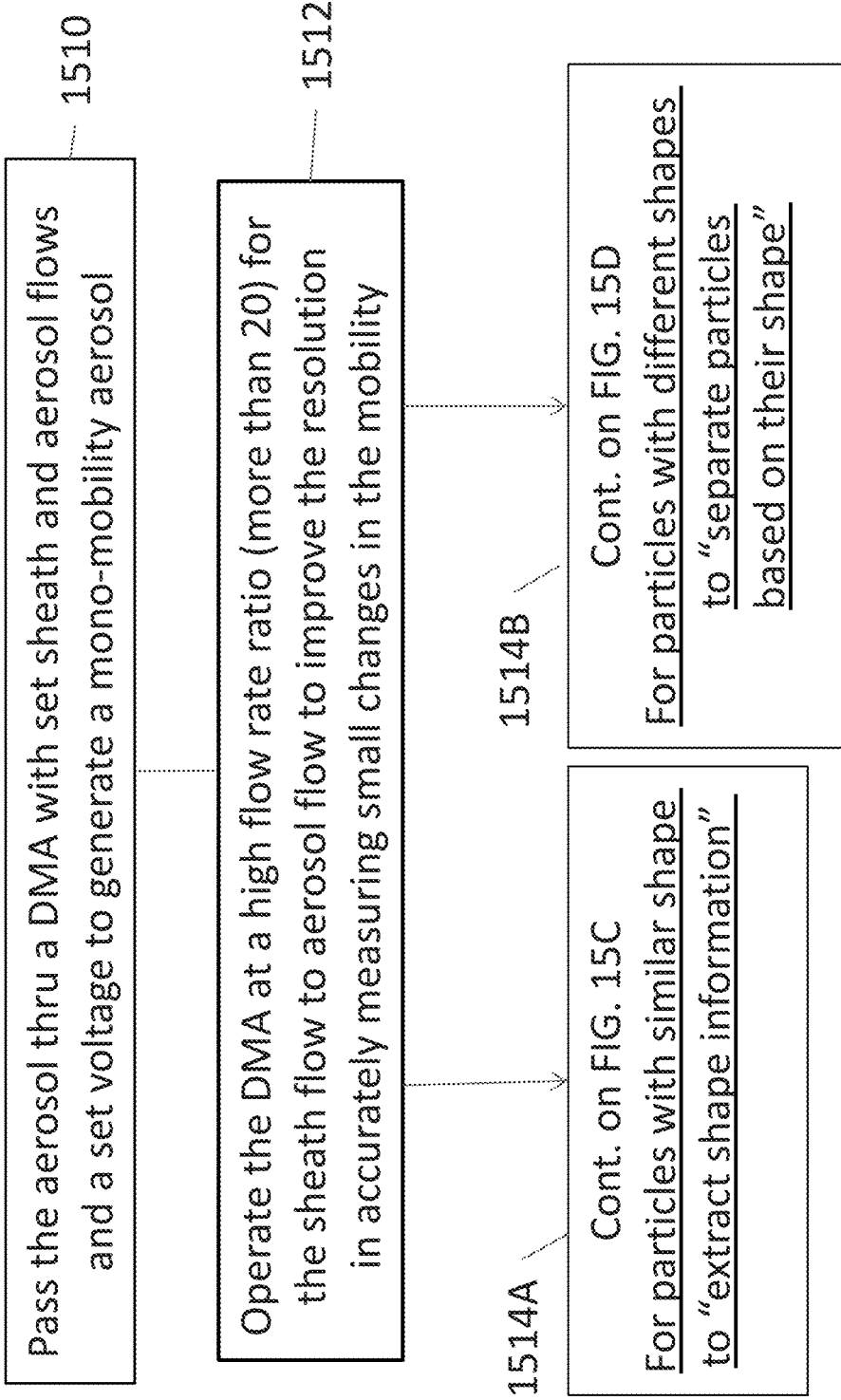
FIG. 15B is continuation of the block diagram of FIG. 15A.

FIGS. 15A and 15B are block diagrams of the method 1500 according to embodiments of the present disclosure of detailed steps of applying the tandem DMA and PFDMA system of FIGS. 5, 5A and 5B1, 5B2, 5B3 For particles with similar shape to "extract shape information and of FIGS. 10, 10A and 10B.

Step 1502 includes calibrating DMAs using standard polystyrene latex (PSL) spheres so that the particle mobility is accurately known to enable accurate measurement of small changes in the mobility.

Step 1504 includes calibrating PFDMA using standard polystyrene latex (PSL) spheres for validating performance of PFDMA (mobility should be independent of pulse frequency).

Step 1506 includes generating a steady state aerosol concentration.

Step 1508 includes passing aerosol thru a bipolar charger (neutralizer) to produce a known charge distribution.

Step 1510 includes passing the aerosol thru a DMA with set sheath and aerosol flows and a set voltage to generate a mono-mobility aerosol.

Step 1512 includes operating the DMA at a high flow rate ratio (more than 20) for the sheath flow to aerosol flow to improve the resolution in accurately measuring small changes in the mobility.

FIG. 15C is a continuation of the block diagram of FIG. 15B for particles with similar shape to extract shape information by applying the tandem DMA and PFDMA system of FIGS. 5, 5A and 5B1, 5B2, 5B3.

In FIGS. 15B and 15C, for 1514A "For particles with similar shape, applying tandem DMA-PFDMA to "extract shape information", step 1516A includes measuring mobility as a function of electric field by varying the duty cycle of the pulse in the PFDMA.

Step 1518A includes fitting the measured mobility data at various electric fields to orientation-averaged mobility model to obtain the shape information.

FIG. 15D is a continuation of the block diagram of FIG. 15B for particles with different shapes to separate particles based on their shape by applying the tandem DMA and PFDMA system of FIGS. 10,10A and 10B.

In FIGS. 15B and 15D, for 1514B "For particles with different shapes, applying tandem DMA-PFDMA to "separate particles based on their shape", step 1516B includes adjusting the duty cycle of the pulse in the PFDMA to reach a higher or lower electric field than the previous DMA.

Step 1518B includes separating particles based on their shape.

Figure 16A:
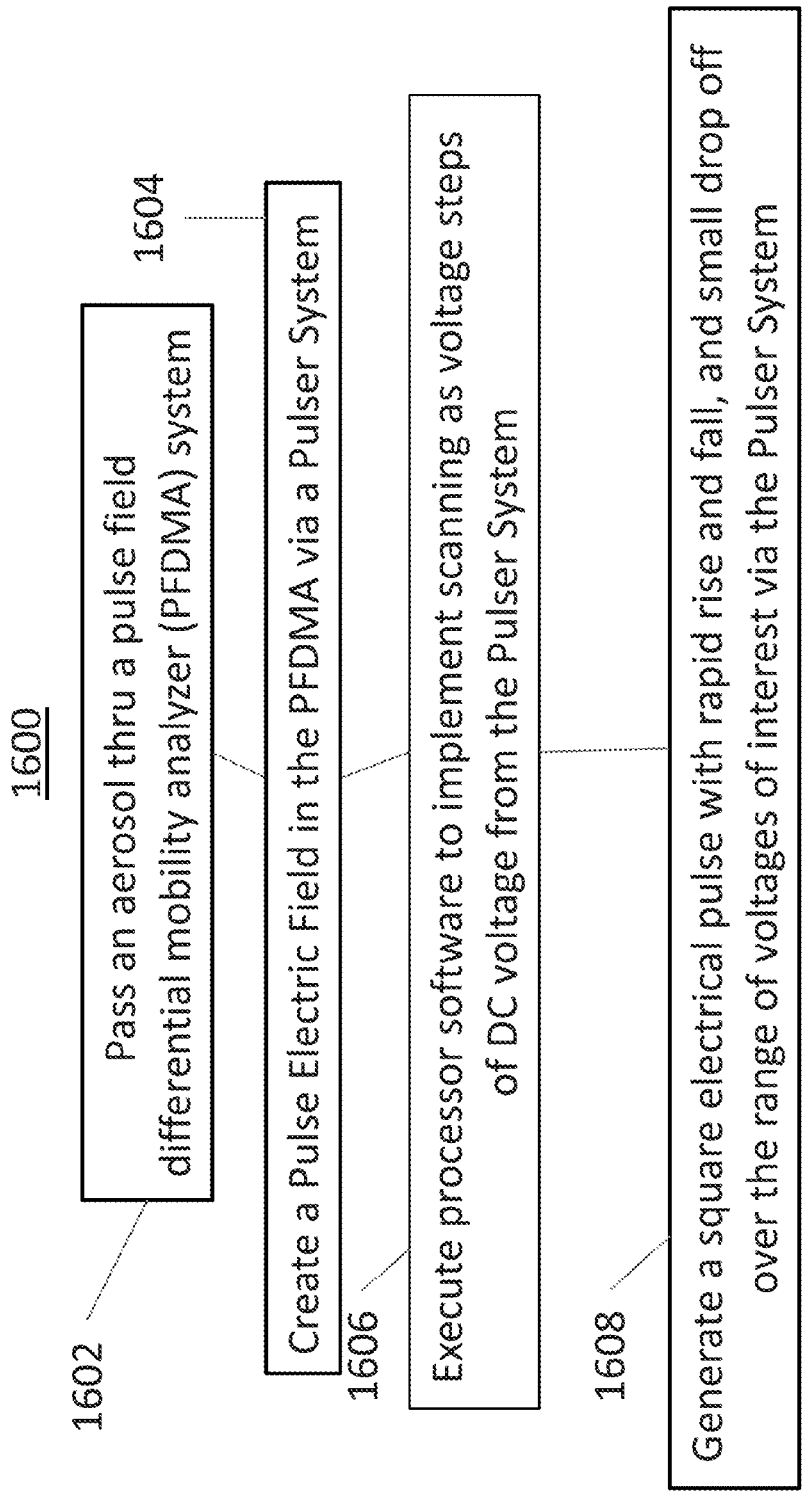
FIG. 16A is a block diagram of the method according to embodiments of the present disclosure of detailed steps of operating the PFDMA system of FIGS. 5, 5A and 5B1, 5B2, 5B3 and of FIGS. 10, 10A and 10B.
Figure 16B:
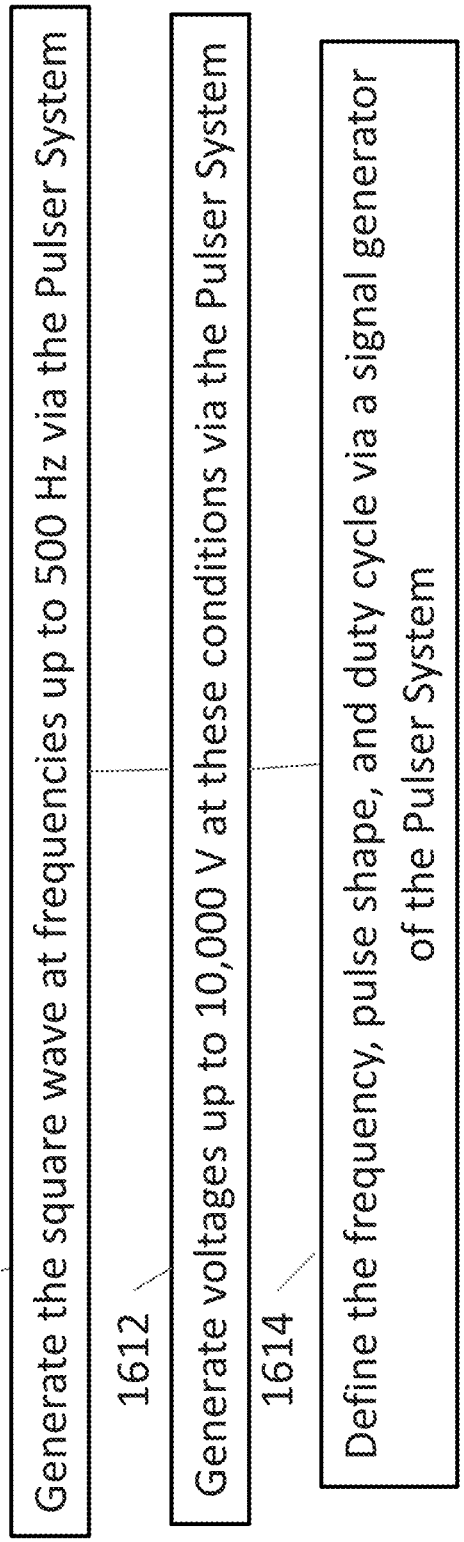
FIG. 16B is continuation of the block diagram of FIG. 16A.

FIGS. 16A and 16B are block diagrams of the method 1600 according to embodiments of the present disclosure of detailed steps of operating the PFDMA system of FIGS. 5, 5A and 5B1, 5B2, 5B3 and of FIGS. 10, 10A and 10B.

Step 1602 includes passing the aerosol thru the PFDMA.

Step 1604 includes creating a Pulse Electric Field in the PFDMA via the Pulser System.

Step 1606 includes executing processor software to implement scanning as voltage steps the DC voltage from the power supply.

Step 1608 includes generating a square electrical pulse with rapid rise and fall, and small drop off over the range of voltages of interest via the Pulser System.

Step 1610 includes generating the square wave at frequencies up to 500 Hz via the Pulser System.

Step 1612 includes generating voltages up to 10,000 V at these conditions via the Pulser System.

Step 1614 includes defining the frequency, pulse shape, and duty cycle via the signal generator of the Pulser System.

5. Conclusion

The development and implementation of a pulsed field-DMA to extract non-spherical shape parameters has been demonstrated. By using pulsed fields that can orient non-spherical particles a systematic change in mobility can be obtained, relative to an equivalent sphere. From this orientation effect particle shape can be deduced (Li et al. 2012). The instrument was validated with PSL spheres with precisely known size, and gold rods with their dimensions determined by TEM. As a demonstration of potential application it has been shown how to determine both length and diameter for rod-like particles. The generic approach can be used to obtain dynamic shape factors or other multi-variate dimensional information (e.g. length and diameter). Another potential application for PFDMA is to separate particle based on their shapes.

Thus the tandem DMA and PFDMA system provides greatly advantageous benefits in determining particle size and shape information for separation for measurements on different types of particles that are currently measured by conventional DMA techniques.

While several embodiments and methodologies of the present disclosure have been described and shown in the drawings, it is not intended that the present disclosure be limited thereto, as it is intended that the present disclosure be as broad in scope as the art will allow and that the specification be read likewise. Therefore, the above description should not be construed as limiting, but merely as exemplifications of particular embodiments and methodologies. Those skilled in the art will envision other modifications within the scope of the claims appended hereto.

LIST OF REFERENCES

The following references are hereby incorporated by reference in their entirety:

Alkilany, A. M., Thompson, L. B., Boulos, S. P., Sisco, P. N. and Murphy, C. J. (2012). Gold nanorods: Their potential for photothermal therapeutics and drug delivery, tempered by the complexity of their biological interactions. *Advanced Drug Delivery Reviews* 64:190-199.

Allen, M. D. and Raabe, O. G. (1985). Slip Correction Measurements of Spherical Solid Aerosol-Particles in an Improved Millikan Apparatus. *Aerosol Sci Tech* 4:269-286.

Cheng, M. T., Xie, G. W., Yang, M. and Shaw, D. T. (1991). Experimental Characterization of Chain-Aggregate Aerosol by Electrooptic Scattering. *Aerosol Sci Tech* 14:74-81.

Colbeck, I., Atkinson, B. and Johar, Y. (1997). The morphology and optical properties of soot produced by different fuels. *J Aerosol Sci* 28:715-723.

Dahneke, B. E. (1973). Slip correction factors for nonspherical bodies—II free molecule flow. *J Aerosol Sci* 4:147-161

Flagan, R. C. (2008). Differential Mobility Analysis of Aerosols: A Tutorial. *Kona Powder Part J* 26:254-268.

Guha, S., Li, M., Tarlov, M. J. and Zachariah, M. R. (2012). Electrospray-differential mobility analysis of bionanoparticles. *Trends in Biotechnology* 30:291-300.

Kim, S. H., Mulholland, G. W. and Zachariah, M. R. (2007). Understanding ion-mobility and transport properties of aerosol nanowires. *J Aerosol Sci* 38:823-842.

Kousaka, Y., Endo, Y., Ichitsubo, H. and Alonso, M. (1996). Orientation-specific dynamic shape factors for doublets and triplets of spheres in the transition regime. *Aerosol Sci Tech* 24:36-44.

Li, M. (2012). Quantifying Particle Properties from Ion-Mobility Measurements, in *Chemical Physics Program*, Dissertation, University of Maryland, College Park. Available online at: http://hdl.handle.net/1903/13627.

Li, M., Guha, S., Zangmeister, R., Tarlov, M. J. and Zachariah, M. R. (2011a). Quantification and Compensation of Nonspecific Analyte Aggregation in Electrospray Sampling. *Aerosol Sci Tech* 45:849-860.

Li, M., Guha, S., Zangmeister, R., Tarlov, M. J. and Zachariah, M. R. (2011b). Method for determining the absolute number concentration of nanoparticles from electrospray sources. *Langmuir* 27:14732-14739.

Li, M., Mulholland, G. W. and Zachariah, M. R. (2012). The Effect of Orientation on the Mobility and Dynamic Shape Factor of Charged Axially Symmetric Particles in an Electric Field. *Aerosol Sci Tech,* 46:1035-1044.

Li, M., You, R., Mulholland, G. W. and Zachariah, M. R. (2013). Evaluating the Mobility of Nanorods in Electric Fields. *Aerosol Sci. Tech.,* 47: 1101-1107.

Li, M.; Mulholland, G. W. and Zachariah, M. R. (2014a). Understanding the mobility of nonspherical particles in the free molecular regime, *Physical Review E.* 89, 022112.

Li, M.; Mulholland, G. W. and Zachariah, M. R. (2014b). Rotational diffusion coefficient (or rotational mobility) of a nanorod in the free-molecular regime. *Aerosol Sci Tech.* 48:2, 139-141.

Ni, W., Kou, X., Yang, Z. and Wang, J. F. (2008). Tailoring longitudinal surface plasmon wavelengths, scattering and absorption cross sections of gold nanorods. *Acs Nano* 2:677-686.

Schmid, G. and Chi, L. F. (1998). Metal clusters and colloids. *Adv Mater* 10:515-526.

Weiss, R. E., Kapustin, V. N. and Hobbs, P. V. (1992). Chain-Aggregate Aerosols in Smoke from the Kuwait Oil Fires. *J Geophys Res-Atmos* 97:14527-14531.

Song, D. K., Lenggoro, I. W., Hayashi, Y., Okuyama, K. and Kim, S. S. (2005). Changes in the shape and mobility of colloidal gold nanorods with electrospray and differential mobility analyzer methods. *Langmuir* 21:10375-10382.

Zelenyuk, A. and Imre, D. (2007). On the effect of particle alignment in the DMA. *Aerosol Sci Tech* 41:112-124.

What is claimed is:

1. A method for extracting shape information for particles with similar shape comprising:
   in a tandem differential mobility analyzer (DMA) and pulse field differential mobility analyzer (PFDMA) system,
      generating a steady state aerosol concentration;
      passing an aerosol flow from the aerosol concentration thru a bipolar charger to produce a known charge distribution;
      passing the aerosol thru a DMA with set sheath and aerosol flows and a set voltage to generate a mono-mobility aerosol;
      passing the mono-mobility aerosol thru a PFDMA system; and
      measuring mobility as a function of electric field by varying the duty cycle of the pulse in the PFDMA system.

2. The method according to claim 1, further comprising fitting the measured mobility data at various electric fields to an orientation-averaged mobility model to obtain the shape information.

3. The method according to claim 1, further comprising, prior to generating the steady state aerosol distribution,
   calibrating the DMA using standard polystyrene latex (PSL) spheres for determination of particle mobility.

4. The method according to claim 1, further comprising, prior to generating the steady state aerosol distribution,
   calibrating the PFDMA system using standard polystyrene latex (PSL) spheres for validating performance of the PFDMA system wherein mobility is independent of pulse frequency.

5. The method according to claim 1, wherein with respect to passing the aerosol through the DMA, the method includes operating the DMA at a high flow rate ratio (more than 20) for
   the sheath flow to aerosol flow to improve the resolution in accurately measuring small changes in the mobility.

6. A method for separating particles with different shapes comprising:
   in a tandem differential mobility analyzer (DMA) and pulse field differential mobility analyzer (PFDMA) system,
   generating a steady state aerosol concentration;
   passing an aerosol flow from the aerosol concentration thru a bipolar charger to produce a known charge distribution;
   passing the aerosol thru a DMA with set sheath and aerosol flows and a set voltage to generate a mono-mobility aerosol;
   passing the mono-mobility aerosol thru a PFDMA system;
   adjusting the duty cycle of the pulse in the PFDMA to reach a higher or lower electric field than in the DMA in which the mono-mobility aerosol was generated; and
   separating particles based on their shape.

7. The method according to claim 6, further comprising, prior to generating the steady state aerosol distribution,
   calibrating the DMA using standard polystyrene latex (PSL) spheres for determination of particle mobility.

8. The method according to claim 6, further comprising, prior to generating the steady state aerosol distribution, calibrating the PFDMA system using standard polystyrene latex (PSL) spheres for validating performance of the PFDMA system wherein mobility is independent of pulse frequency.

* * * * *